(12) United States Patent
Sharpe et al.

(10) Patent No.: US 6,819,411 B1
(45) Date of Patent: Nov. 16, 2004

(54) OPTICAL APPARATUS

(75) Inventors: Johnathan Sharpe, Fort Collins, CO (US); Peter Niven Schaare, Hamilton (NZ)

(73) Assignee: XY, Inc., Fort Collins, CO (US)

( * ) Notice: Subject to any disclaimer, the term of this patent is extended or adjusted under 35 U.S.C. 154(b) by 0 days.

(21) Appl. No.: 09/355,461
(22) PCT Filed: Feb. 2, 1998
(86) PCT No.: PCT/NZ98/00009
§ 371 (c)(1), (2), (4) Date: Sep. 17, 1999
(87) PCT Pub. No.: WO98/34094
PCT Pub. Date: Aug. 6, 1998

(30) Foreign Application Priority Data

Jan. 31, 1997 (NZ) ............................................. 314169

(51) Int. Cl.⁷ .................... G01N 21/00; G01N 21/64; G01J 3/30
(52) U.S. Cl. .................... 356/72; 356/317; 356/337; 250/461.2
(58) Field of Search ............ 356/72, 317–318, 356/336–343, 246, 446; 250/461.2

(56) References Cited

U.S. PATENT DOCUMENTS

| | | | |
|---|---|---|---|
| 3,299,354 A | 1/1967 | Hogg | 207/582 |
| 3,547,526 A | 12/1970 | Devereux | 350/200 |
| 3,661,460 A | 5/1972 | Elking et al. | 356/36 |
| 3,710,933 A | 1/1973 | Fulwyler et al. | 209/3 |
| 3,761,941 A | 9/1973 | Robertson | 346/1 |
| 3,810,010 A | 5/1974 | Thom | 324/71 |
| 3,826,364 A | 7/1974 | Bonner et al. | 209/3 |
| 3,833,796 A | 9/1974 | Fetner et al. | 235/151.3 |

(List continued on next page.)

FOREIGN PATENT DOCUMENTS

| | | | |
|---|---|---|---|
| EP | 025296 A2 | 3/1981 | G01N/15/07 |
| EP | 0160201 A2 | 11/1985 | G01N/15/14 |

(List continued on next page.)

OTHER PUBLICATIONS

Celestron Telescope Basics http://www.celestron.com/tb–2ref.htm printed Jan. 6, 2003; 4 pages.

(List continued on next page.)

Primary Examiner—Frank G. Font
Assistant Examiner—Amanda Merlino
(74) Attorney, Agent, or Firm—Santangelo Law Offices, P.C.

(57) ABSTRACT

Various optical apparatus provide a source of parallel light (7, 75). The parallel light (7, 75) is generally achieved by directing an incident beam at the apex of a prism (1, 22, 24, 26, 28). The prism may have varying configurations. One configuration has a forward conical face (24). Another configuration has a pyramidal forward end (22). Other configurations are also disclosed. The application also discloses the use of reflectors (20, 78, 216, 316, 400) having internal reflective surfaces shaped as three-dimensional figures of revolution, for example paraboloid or ellipsoid. The reflectors (20, 78, 216, 316) focus light incident onto the reflectors at one or more foci (F, 220, 320, 420). The reflectors may be used in combination with the optical apparatus including the prisms (1, 22, 24, 26, 28). The reflectors (20, 78, 216, 316) may be used in flow cytometers for focussing light at a sample stream (237, 337) passing through the focus (F, 220, 320, 420) of the reflector (20, 78, 216, 316). The collection of scattered and/or fluorescent light from an illuminated sample stream (237, 337) in a flow cytometer may be achieved with the use of a collector shaped as a figure of revolution e.g. paraboloid or ellipsoid. Various optical methods and methods for flow cytometry are also disclosed.

5 Claims, 11 Drawing Sheets

U.S. PATENT DOCUMENTS

| | | |
|---|---|---|
| 3,909,744 A | 9/1975 | Wisner et al. ............. 331/94.5 |
| 3,947,093 A | 3/1976 | Goshima et al. ............ 350/189 |
| 3,960,449 A | 6/1976 | Carleton et al. ............ 356/103 |
| 3,963,606 A | 6/1976 | Hogg ............................ 209/3 |
| 3,973,196 A | 8/1976 | Hogg ........................... 324/71 |
| 4,014,611 A | 3/1977 | Simpson et al. .............. 356/72 |
| 4,070,617 A | 1/1978 | Kachel et al. ................ 324/71 |
| 4,162,282 A | 7/1979 | Fulwyler et al. ............... 264/9 |
| 4,179,218 A | 12/1979 | Erdmann et al. ........... 356/336 |
| 4,200,802 A | 4/1980 | Salzman et al. ........ 250/461 B |
| 4,230,558 A | 10/1980 | Fulwyler .................... 209/3.1 |
| 4,255,021 A | 3/1981 | Brunsden ................... 350/286 |
| 4,274,740 A | 6/1981 | Eidenschink et al. ....... 356/336 |
| 4,302,166 A | 11/1981 | Fulwyler et al. ............... 425/6 |
| 4,317,520 A | 3/1982 | Lombardo et al. ........... 209/3.1 |
| 4,318,480 A | 3/1982 | Lombardo et al. ........... 209/3.1 |
| 4,318,481 A | 3/1982 | Lombardo et al. ........... 209/3.1 |
| 4,318,482 A | 3/1982 | Barry et al. ................. 209/3.1 |
| 4,318,483 A | 3/1982 | Lombardo et al. ........... 209/3.1 |
| 4,325,483 A | 4/1982 | Lombardo et al. ........... 209/3.1 |
| 4,341,471 A | 7/1982 | Hogg et al. ................. 356/343 |
| 4,350,410 A | 9/1982 | Minott ....................... 350/170 |
| 4,361,400 A | 11/1982 | Gray et al. ................... 356/23 |
| 4,395,676 A | 7/1983 | Hollinger et al. .......... 324/71.4 |
| 4,400,764 A | 8/1983 | Kenyon ...................... 362/263 |
| 4,422,761 A | 12/1983 | Frommer .................... 356/338 |
| 4,487,320 A | 12/1984 | Auer ......................... 209/3.1 |
| 4,498,766 A | 2/1985 | Unterleitner ................. 356/73 |
| 4,515,274 A | 5/1985 | Hollinger et al. ............ 209/3.1 |
| 4,523,809 A | 6/1985 | Toboada et al. ............ 350/163 |
| 4,538,733 A | 9/1985 | Hoffman .................... 209/3.1 |
| 4,598,408 A | 7/1986 | O'Keefe ...................... 372/94 |
| 4,600,302 A | 7/1986 | Sage, Jr. ...................... 356/39 |
| 4,631,483 A | 12/1986 | Proni et al. ................. 324/71.4 |
| 4,637,691 A | 1/1987 | Uehara et al. .............. 350/432 |
| 4,673,288 A | 6/1987 | Thomas et al. ............... 356/72 |
| 4,691,829 A | 9/1987 | Auer ........................... 209/3.1 |
| 4,702,598 A | 10/1987 | Böhmer ...................... 356/343 |
| 4,744,090 A | 5/1988 | Freiberg ....................... 372/94 |
| 4,758,729 A | 7/1988 | Monnin ...................... 250/560 |
| 4,794,086 A | 12/1988 | Kasper et al. ................ 436/36 |
| 4,818,103 A | 4/1989 | Thomas et al. ............... 356/72 |
| 4,831,385 A | 5/1989 | Archer et al. ................ 346/1.1 |
| 4,845,025 A | 7/1989 | Lary et al. ..................... 435/2 |
| 4,942,305 A | 7/1990 | Sommer ..................... 250/574 |
| 4,981,580 A | 1/1991 | Auer ........................... 209/3.1 |
| 4,983,038 A | 1/1991 | Ohki et al. .................. 356/246 |
| 5,005,981 A | 4/1991 | Schulte et al. .............. 366/219 |
| 5,007,732 A | 4/1991 | Ohki et al. ................... 356/73 |
| 5,030,002 A | 7/1991 | North, Jr. .................... 356/73 |
| 5,079,959 A | 1/1992 | Miyake et al. ........... 73/864.85 |
| 5,098,657 A | 3/1992 | Blackford et al. ............ 422/73 |
| 5,101,978 A | 4/1992 | Marcus ...................... 209/3.1 |
| 5,127,729 A | 7/1992 | Oetliker et al. ............. 356/317 |
| 5,132,548 A | 7/1992 | Borden et al. .............. 250/574 |
| 5,144,224 A | 9/1992 | Larsen ...................... 324/71.4 |
| 5,150,313 A | 9/1992 | Van den Engh et al. .... 364/569 |
| 5,159,397 A | 10/1992 | Kosaka et al. ................ 356/73 |
| 5,159,403 A | 10/1992 | Kosaka ....................... 356/243 |
| 5,167,926 A | 12/1992 | Kimura et al. ................ 422/67 |
| 5,180,065 A | 1/1993 | Touge et al. ................ 209/577 |
| 5,182,617 A | 1/1993 | Yoneyama et al. ......... 356/440 |
| 5,199,576 A | 4/1993 | Corio et al. ................ 209/564 |
| 5,215,376 A | 6/1993 | Schulte et al. .............. 366/348 |
| 5,247,339 A | 9/1993 | Ogino ......................... 356/73 |
| 5,259,593 A | 11/1993 | Orme et al. .................. 266/78 |
| 5,260,764 A | 11/1993 | Fukuda et al. ................ 356/73 |
| 5,298,967 A | 3/1994 | Wells ......................... 356/336 |
| 5,359,907 A | 11/1994 | Baker et al. ............... 73/865.5 |
| 5,370,842 A | 12/1994 | Miyazaki et al. ........ 422/82.06 |
| 5,412,466 A | 5/1995 | Ogino ........................ 356/246 |
| 5,452,054 A | 9/1995 | Dewa et al. .................. 355/67 |
| 5,466,572 A | 11/1995 | Sasaki et al. .................. 435/2 |
| 5,467,189 A | 11/1995 | Kreikebaum et al. ....... 356/336 |
| 5,471,299 A | 11/1995 | Kaye et al. ................. 356/336 |
| 5,483,469 A | 1/1996 | Van den Engh et al. .... 364/555 |
| 5,558,998 A | 9/1996 | Hammond et al. ............ 435/6 |
| 5,596,401 A | 1/1997 | Kusuzawa .................... 356/23 |
| 5,601,235 A | 2/1997 | Booker et al. ................ 239/4 |
| 5,602,349 A | 2/1997 | Van den Engh ......... 73/864.85 |
| 5,641,457 A | 6/1997 | Vardanega et al. ...... 422/82.01 |
| 5,643,796 A | 7/1997 | Van den Engh et al. ...... 436/50 |
| 5,650,847 A | 7/1997 | Maltsev et al. ............. 356/336 |
| 5,675,401 A | 10/1997 | Wangler et al. ............... 355/67 |
| 5,684,575 A | 11/1997 | Steen ........................... 356/7 |
| 5,700,692 A | 12/1997 | Sweet ......................... 436/50 |
| 5,707,808 A | 1/1998 | Roslaniec et al. ............. 435/6 |
| 5,708,868 A | 1/1998 | Ishikawa ..................... 396/71 |

FOREIGN PATENT DOCUMENTS

| | | | | |
|---|---|---|---|---|
| EP | 0468100 A1 | 1/1992 | ......... | G01N/15/14 |
| FR | 2699678 A1 | 12/1992 | ......... | G01N/21/64 |
| JP | 61139747 A | 6/1986 | ......... | G01N/21/53 |
| JP | 61159135 A | 7/1986 | ......... | G01N/21/17 |
| JP | 2024535 | 1/1990 | ......... | G01N/15/14 |
| JP | 4126064 A | 4/1992 | ............ | A23P/1/08 |
| JP | 4126065 A | 4/1992 | ............ | A23P/1/12 |
| JP | 4126066 A | 4/1992 | ............ | C12M/1/02 |
| JP | 4126079 A | 4/1992 | ............ | C12N/9/48 |
| JP | 4126080 A | 4/1992 | ............ | C12N/9/90 |
| JP | 4126081 A | 4/1992 | ......... | C12N/15/02 |
| RU | 1260778 A1 | 9/1986 | ......... | G01N/21/64 |
| SU | 1056008 | 11/1983 | ......... | G01N/21/24 |
| US | WO 98/34094 | 8/1998 | | |

OTHER PUBLICATIONS

Sharpe, John C. et al, "A new optical configuration for flow cytometric sorting of aspherical cells", Horticulture and Food Research Institute of New Zealand Ltd., Hamilton, New Zealand (PNS) Nov. 2, 1997.

Flow Cytometry and Cell Sorting, A. Radbruch (Ed.), "Operation of a Flow Cytometer" by Gottlinger et al., 1992, pp. 7–23.

Flow Cytometry: Instrumentation and Data Analysis, Van Dilla et al. (Eds.), "Overview of Flow Cytometry: Instrumentation and Data Analysis" by Martin Van Dilla, 1985, pp. 1–8.

Flow Cytometry: Instrumentation and Data Analysis, Van Dilla et al. (Eds.), "Flow Chambers and Sample Handling," by Pinkel et al., 1985, pp. 77–128.

An Historical Review of the Development of Flow Cytometers and Sorters, Melamed et al, 1979, pp. 3–9.

Axicon; Journal of the Optical Society of America; vol. 44, #8, Eastman Kodak Company, Hawk–Eye Works, Rochester, NY, Sep. 10, 1953, pp. 592–597.

Johnathan Sharpe's thesis; "An Introduction of Flow Cytometry," Chptr. 2–2.2, 1997.

Johnathan Sharpe's thesis; "Gender Preselection–Principle Scientific Options," Chpter. 3.4–3.4.8, 1997.

Johnathan Sharpe's thesis; "Sperm Sexing using Flow Cytometry," Chpter. 3.5–3.5.8, 1997.

Johnathan Sharpe's thesis; "Sperm Sexing–Method of Johnson et al.," Chpter. 3.6–4.3.4, 1997.

Lawrence A. Johnson, Sex Preselection by Flow Cytometric Separation of X and Y Chromosome–bearing Sperm based on DNA Difference: a Review, Reprod. Fertil. Dev., 1995, 7, pp. 893–903.

M.J. Skogen–Hagenson, et al; "A High Efficiency Flow Cytometer," The Journal of Histochemistry and Cytochemistry, vol. 25, No. 7, pp. 784–789, 1977, USA.

D.L. Garner, et al; Quantification of the X– and Y– Chromosome–Bearing Spermatozoa of Domestic Animals by Flow Cytometry[1], Biology of Reproduction 28, pp. 312–321, (1983).

OPTICAL APPARATUS

TECHNICAL FIELD

This invention relates to an optical apparatus. In particular, although not exclusively, this invention has application to the field of flow cytometry. However, it is to be understood that several of the inventive aspects have application beyond flow cytometry and may have broad application in the field of optics generally. For example, several aspects of the invention may be used in photometry or optical particle detection apparatus.

BACKGROUND ART

Generally when illuminating a particle or an object for analysis, the light source is directed onto the particle from a single direction. An analysis may be made of light reflected or produced by the particle eg. fluorescence to reveal certain properties of the particle. The particular portion of the particle illuminated depends on the orientation of the particle with respect to the light source. Where the particle or object is asymmetrical, the light measurements will vary depending on which portion is illuminated, making it difficult to analyse the particle or object as a whole.

Such difficulties are encountered in flow cytometry since it is common for particles being analysed to be asymmetrical eg. mammalian spermatozoa.

Flow cytometers are often used to measure the properties of cells or particles which are carried in a stream of fluid. The stream is generally comprised of a sheath fluid into the centre of which is injected a narrow aqueous suspension of cells/particles. The sheath fluid focuses the sample cells/particles into single file. The stream containing the particles/cells passes through an inspection point which is the focus of an intense light beam. The particles/cells may have been stained with a light—sensitive stain which when illuminated, will absorb the incident light and fluoresce. Light scatters off the particles and/or alternatively causes fluorescence. This scattered or fluorescent light is then measured by a detector generally aligned with the incident beam. The characteristics of the detected signal(s) such as peak intensity, peak area or other characteristics of interest may then be used to derive properties of the particle, for example size.

In a flow cytometer with sorting capability (as opposed to a purely analytical instrument) the detected signal(s) may be used to trigger sorting hardware which can be programmed to divert droplets from the stream of fluid. The sorting criteria will vary with the application, for example, the sorting may be conducted according to size or, in the case of spermatozoa, the DNA content of the cell.

One problem with conventional flow cytometers is that particle asymmetry often renders the optical characteristics of a particle difficult to measure. For example, a flat particle can pass through the inspection point with a random orientation. Thus, the intensity of the resultant scattered or fluorescent light may vary according to particle orientation and the detectors will measure different light intensities at different locations.

Thus, particle asymmetry can lead to a reduced resolution of measurement of the particles. It follows that, in cytometers with a sorting capability, this reduced resolution in measurement of the particles results in a decreased ability to accurately separate populations of cells with different optical properties. Such a problem is encountered in separation of male and female mammalian sperm.

In mammals, sperm carry the sex determining chromosomes and the total DNA content found in male and female sperm may differ. For example, in cattle the difference in the DNA content between male and female sperm is approximately 4%. This difference in DNA provides a means by which sperm may be separated in a sorting flow cytometer, making a predetermination of an offspring's sex possible when artificial breeding of animals is carried out. Utilising such a technique in artificial breeding would offer considerable economic advantages in livestock management, but is currently made difficult by the asymmetric geometry of the flat sperm head. As an example, bull sperm are flat cells with head dimensions of approximately 10 microns by 4 microns by 1 micron attached to a 40 micron flagellum. The asymmetric properties of the bull sperm head result in a high variation in both scattered light and fluorescent light emission with sperm orientation. In particular, fluorescent emission varies by a factor of two with sperm orientation (see DNA Contention Measurements of Mammalian Sperm. CYTOMETRY 3:1–9[1982]), effectively masking the 4% variation in intensity due to the sex of the sperm.

A number of flow cytometric systems have been developed in an attempt to overcome the problems encountered when analysing asymmetric particles such as sperm cells.

One flow cytometric system that has been developed in an attempt to overcome this problem introduces asymmetric cells travelling in a slow moving stream into the middle of a fast flowing sheath stream. Hydrodynamics then tends to align the asymmetric cells with their long axis parallel to the direction of the fast flowing sheath stream.

While this approach tends to reduce the vertical variation of light intensity from asymmetric particles, the radial variation remains. This system has been further refined so as to further reduce the orientation-related variation in the detected light intensity of particles.

The system developed by Pinkel et al (see Flow Cytometry in Mammalian Sperm: Progress Morphology and DNA Measurement. THE JOURNAL OF HISTOCHEMISTRY AND CYTOCHEMISTRY 24:353–358[1979]), showed that the orientation of bull sperm could be further aligned by bevelling the end of the tube which injected the sample stream (ie. that which contains the sperm) into the sheath flow.

The system which attempted to overcome the problems of flow cytometric analysis of asymmetric cells was that described by Johnson (see Sex Preselection by Flow Cytometric Separation of X AND Y Chromosome Bearing Sperm Based on DNA Difference: A review. REPRODUCTIVE FERTILITY DEVELOPMENTS 7:893–903[1995]), in relation to separation of bull sperm by sex. Johnson's approach utilised two detectors; one in line with the illuminating laser beam (the 0 degree detector) and one at right angles to the beam (the 90 degree detector). Sperm emit fluorescence preferentially through their narrow edges. Johnson determined which sperm were aligned edge-on to the 90 degree detector by detecting the bright emission from their edges, and used the 0 degree detector for measuring the flat-face emission from only the aligned sperm.

However, this system still had a number of drawbacks. One drawback was that it was a requirement for this system that the sample flow be moving slowly with respect to the sheath flow, thereby reducing sample throughput. A further drawback was that it only produces good alignment at very low flow rates. At the optimal flow rate, which produced the greatest number of aligned cells per second, only 40% of cells were aligned. Thus, the number of aligned cells had been increased from 10% to 40%, but approximately 60% of the cells remained unaligned, and further, due to the requirement of a low flow rate, there was a reduction in system throughput.

It will be appreciated that the rejection of unaligned cells again reduces the processing rate of this system and unnecessarily wastes sperm cells.

One system which moved towards radial light collection was the Ellipsoidal Collector described by Skogen-Hagenson et al (see A High Efficiency Flow Cytometer, CYTOCHEMISTRY 25:784–789[1977]), who developed a light collection system based on a hollow "egg shaped" brass reflector. The reflector surface was elliptical in cross-section and light from the inspection point at one focus was collected at the second focus. This system was demonstrated to have an ability to reduce the orientation dependence observed with bull sperm.

However, it still had orientation dependent illumination, (ie. Light source coming from a single direction). A further problem with this system is that it is unable to provide a particle sort function (ie. according to sperm sex).

A further system which implemented both symmetric illumination and symmetric light collection was the Epi-Illumination system described by Garner et al (see Quantification of the X and Y Chromosome Bearing Spermatozoa of Domestic Animals by Flow Cytometry, BIOLOGY OF REPRODUCTION 28:312–321[1983]). In this system the sample stream travelled directly towards a high numerical index microscope objective lens and was diverted sideways after the stream had passed through the focal point of the lens. Illumination was delivered through the lens and light was collected back through the lens.

While this system also demonstrated a good ability to eliminate the orientation dependencies of bull sperm, it was also incapable of modification for high speed sorting. This was due to its sideways diversion of the sperm immediately after passing through the focal point.

Earlier systems have also relied on laser light, because of the intensity of laser light sources. Unfortunately, such laser systems can be quite expensive and only add to the cost of devices such as flow cytometers. Because lasers typically deliver a single wavelength of light, use of lasers also has made it difficult to utilise a single light source to provide a variety of wavelengths of light, e.g. in conjunction with filters that filter out all but the desired wavelengths.

Furthermore, previous systems have often required the precise alignment of optics in order to accomplish a proper delivery of electromagnetic radiation onto the cell under analysation or collection of fluorescence emitted by a cell. This can be a tedious process that adds to the expense of the analysation instruments. Hence, there is a need for a system, e.g., in flow cytometry, in which the optics that focus and collect electromagnetic radiation for measurement purposes are quicly and easily established in their proper orientation.

It is an object of the present invention to overcome the afore mentioned shortcomings of known optical apparatus with particular application to flow cytometers. It is also an object of the invention to provide the public with a useful choice.

SUMMARY OF THE INVENTION

In accordance with a first aspect of the present invention there is provided an optical apparatus including: a prism having a conical portion with an apex at a forward end of the prism and a central axis extending through the apex of the prism; an optical arrangement including a source of electromagnetic radiation, the optical arrangement adapted to direct an incident beam of electromagnetic radiation onto the apex of the conical portion in a direction substantially aligned with the central axis of the conical portion; and a reflective surface provided behind the apex of the prism; such that the beam refracted by the prism will be reflected by the reflective surface back through the prism to project from the forward end of the prism as an annular beam of electromagnetic radiation.

The optical apparatus described above thereby serves to produce an annular beam of electromagnetic radiation from a single beam of electromagnetic radiation incident onto the apex of the conical portion. Preferably, the arrangement is such to provide the beam with a constant cross section to produce a cylindrical tube of light. The prism may also include a cylindrical base portion at a rear end thereof which has a circular cross section corresponding to the cross section of the base of the conical portion.

In accordance with a second aspect of the present invention there is provided an optical apparatus including: a prism having a pyramidal portion with an even number of inclined faces meeting at an apex at a forward end of the prism and a central axis extending through the apex an optical arrangement including a source of electromagnetic radiation, the optical arrangement adapted to direct an incident beam of electromagnetic radiation onto the apex of the pyramidal portion in a direction substantially aligned with the central axis of the pyramidal portion; and a reflective surface provided behind the apex of the prism; such that the beam refracted by the prism will be reflected by the reflective surface back through the prism to project from the forward end of the prism as a number of parallel beams.

It is required that the pyramidal portion have an even number of inclined faces since the optical geometry is such that the beams cross the prism to reflect from the opposing face. Apart from this constraint, the number of the inclined faces is not limited. For example, there may be 4, 6, 8 . . . 12 inclined triangular faces converging towards the apex of the pyramidal portion. Preferably, the pyramidal portion also includes a base portion with a cross section corresponding to the base of the pyramidal portion. For example, where the pyramid has four inclined faces an appropriate base portion would be a rectangular prism or a cube.

In either of the first two aspects of the invention, the reflective surface may be provided at the rear end of the prism. However, the invention is not limited to this arrangement and may potentially be disposed within the prism itself. Another preferred arrangement is for the reflective surface to be spaced from the base portion. Another desirable feature is that this spacing be adjustable to provide a variable annular beam diameter. However, where the reflective surface is spaced from the prism the electromagnetic radiation may suffer losses from multiple interface reflection. However, as such a design would have a reduced length from the front to the rear end, the transmission losses would be less than for a longer prism with the reflective surface provided at the rear end.

Suitably the prisms are manufactured from optical glass such as BK7 optical glass. However, where the application is intended for use with UV electromagnetic radiation, it is preferred to manufacture the prism from UV-suitable material such as fused silica. In such an application, it is also desirable that the reflective surface be comprised of a UV-grade mirror to increase the transmission efficiency of the optical apparatus.

As mentioned above, the optical apparatus may be used with ultra-violet radiation, preferably produced from a laser source. The electromagnetic radiation may also include other wavelengths including those in the visible spectrum. Suitably, the incident electromagnetic radiation is in the form of a collimated beam.

The optical apparatus described above in connection with the first two aspects may desirably be used in combination with a paraboloidal reflector having an internal paraboloidal-shaped reflective surface and an optical axis. Such a reflector will be oriented to receive, on its reflective surface, the electromagnetic radiation projected from the forward end of the prism. It will be appreciated that such a paraboloidal shaped reflective surface will have a focus at which all light parallel to the optical axis and incident onto the reflective surface will be directed. In other words, the parallel electromagnetic radiation projected from the prism will be received onto the paraboloidal reflector to converge at the focus. Such a concentration of electromagnetic radiation may have many useful and varied applications in the field of optics. In particular, the invention is capable of providing radially symmetric illumination to the focus of the paraboloidal reflector. The term "radially symmetric" means that for every beam of incident radiation to the focus, a substantially diametrically opposite beam will be incident to the focus. Each beam of the radially symmetric illumination may have the same angle to the optical axis of the paraboloidal reflector. Thus a convergent disc of electromagnetic radiation onto the focus will be included in the definition of "radially symmetric". Such a convergent disc can be achieved through the use of the first-described optical apparatus in combination with the paraboloidal reflector. Any object can be placed at the focus of the paraboloidal reflector for illumination and inspection. As will be discussed with following aspects of the invention, the apparatus has particular application to flow cytometry in that a flow source may be provided to direct particles through the focus of the paraboloidal reflector.

It will be understood that the source of electromagnetic radiation may not be directed directly at the apex of the prism and the invention allows for the use of mirrors and other reflectors as desired. In particular, a second reflector may be disposed between the prism and the paraboloidal reflector, the second reflector having reflective portions to reflect the incident beam from the source onto the apex of the prism and transmitting portions to transmit the beam(s) projected from the forward end of the prism.

However, the invention is not limited to the particular prisms described in the forgoing aspects of the invention. Other optical configurations are envisaged to produce the projected annular beam or parallel beams of electromagnetic radiation. Furthermore, other types of reflectors which focus incident radiation towards one or more foci could be adopted.

Accordingly, a third aspect of the invention provides an optical apparatus including: an optical configuration adapted to produce an annular beam of electromagnetic radiation having a central axis or plurality of beams of electromagnetic radiation wherein said plurality of beams are evenly spaced from a central axis; and a focussing reflector having an internal reflective surface having an optical axis and one or more foci, the reflector being oriented to receive, onto its reflective surface, the annular beam or the plurality of beams of electromagnetic radiation.

For example, the optical element may comprise any known reflective axicons as well as the particular prisms described above which, in some cases are also axicons. For example, the axicon may comprise an inner conical mirror with forward reflective surfaces surrounded by an outer conical mirror with forward reflective surfaces wherein the optical axes of the two mirrors are aligned. The reflective surfaces form the letter "W", hence the name w-axicon or waxicon.

Preferably, the focussing reflector has an internal reflective surface which is paraboloidal in shape. The use of the term "paraboloidal reflector" used throughout the specification and the claims will be understood to mean "a reflector conforming to the shape of a paraboloid of revolution". The term is also to be understood to mean "a portion of a full paraboloid of revolution". Similarly, in regard to the optical axis of a paraboloid, such an axis may also be considered to be the parabolic or central axis of the paraboloid.

As mentioned in connection with the foregoing aspect of the invention, the apparatus may be incorporated into a flow cytometer including a flow source to produce a flow of particles to be analysed in which the flow source is adapted to direct the flow of particles substantially through one of the foci of the reflective surface. Suitably the flow source can be adapted to substantially align the flow with the optical axis of the reflective surface. Moreover, an aperture may be provided in the focussing reflector for passage of the flow therebeyond.

It is desirable that the present invention will be used in a flow cytometer accommodating a sorting function. Thus, the flow means may include a nozzle and the flow cytometer may incorporate electrostatic droplet deflection sorting apparatus below the aperture in the focussing reflector.

In accordance with a fourth aspect of the present invention there is provided an optical method including: providing a prism having a conical portion with an apex at the forward end, a central axis extending through the apex and a reflective surface provided behind the apex of the prism; directing an incident beam of electromagnetic radiation onto the apex of the conical portion in a direction substantially aligned with the central axis of the conical portion to produce an annular beam of electromagnetic radiation projecting from the forward end of the prism.

In accordance with a fifth aspect of the present invention there is provided an optical method including: providing a prism having a pyramidal portion with an even number of inclined faces meeting at an apex at a forward end of the prism, a central axis extending through the apex and a reflective surface provided behind the apex of the prism; directing an incident beam of electromagnetic radiation onto the apex of the pyramidal portion in a direction substantially aligned with the central axis of the pyramidal portion to produce parallel beams of electromagnetic radiation projecting from the forward end of the prism.

In accordance with another aspect of the present invention there is provided an analysation instrument including: a flow source to produce a flow of particles to be analysed, the flow source being adapted to direct the flow of particles through an inspection zone; an optical arrangement including a source of electromagnetic radiation, the optical arrangement adapted to converge substantially coplanar, substantially radially symmetric electromagnetic radiation towards the inspection zone.

Preferably, the electromagnetic radiation coverges in the form of a disc disposed symmetrically relative to the central axis.

In accordance with yet another aspect of the present invention there is provided a method of analysing including:

providing a flow of particles to be analysed; directing the flow of particles to be analysed through an inspection zone; converging substantially coplanar, substantially radially symmetric electromagnetic radiation towards the inspection zone.

In accordance with a further aspect of the present invention there is provided an analysation instrument including: a flow source to produce a flow of particles to be analysed; a source of electromagnetic radiation; a reflector adapted to reflect at least a portion of the electromagnetic radiation at the flow of particles to illuminate the flow of particles; an optical configuration including a sensor adapted to sense electromagnetic radiation; wherein the reflector is also adapted to reflect, to the optical configuration, any electromagnetic radiation produced as a result of the illumination of the flow of particles.

Thus the reflector described in accordance with this aspect serves the dual purpose of reflecting the electromagnetic radiation onto the flow of particles as well as collecting the electromagnetic radiation for transmission to the sensor. Such a configuration can be achieved with the use of a reflector having an internal reflective surface which is paraboloidal in shape.

It will be understood that any use of the term "illumination" or "illuminate" is not restricted to merely visible illumination as non-visible wavelengths may also be used. As mentioned previously, in certain applications ultra violet radiation may be used. Furthermore, reference to electromagnetic radiation "produced" by the particle may include any florescence produced by the particles as a result of the incident illumination and/or any light scattered by the particles. It should also be understood that "irradiate" is intended to have the same meaning as "illuminate".

In accordance with a still further aspect of the present invention there is provided a method of analysing including providing: a flow of particles to be analysed; providing a source of electromagnetic radiation; reflecting with a reflector at least a portion of the electromagnetic radiation to illuminate the flow of particles; reflecting with the reflector at least a portion of any electromagnetic radiation produced from the illumination of the flow of particles; sensing a portion of the electromagnetic radiation produced from the illumination of the flow of particles.

In accordance with still a further aspect of the present invention there is provided a flow cytometer including: a flow source to produce a linear flow of particles to be analysed, the flow source being adapted to direct the flow of particles through an inspection zone; an optical arrangement adapted to converge electromagnetic radiation onto the flow at the inspection zone in a radially symmetric manner about the inspection zone; a collector to collect electromagnetic radiation either produced or deflected from the particles in the flow; a processor to derive, from the collected electromagnetic radiation, predetermined information relating to each of at least some of the particles in the flow; and a correlator to correlate the derived information with the associated particle downstream of the inspection zone.

As mentioned previously, the radially symmetric illumination may be provided in the form of a continuous disc convergent towards the inspection zone. Another preferred radially symmetric arrangement of the illumination is in the form of discreet beams converging towards the inspection zone. Either way, the particle is illuminated evenly from all sides.

In accordance with a further aspect of the present invention there is provided a flow cytometer including: a flow source to produce a linear flow of particles to be analysed, the flow source being adapted to direct the flow of particles through an inspection zone; and an optical arrangement including a focussing reflector having an internal reflective surface with one or more foci, the optical arrangement adapted to converge electromagnetic radiation onto the flow of particles at the inspection zone by reflection from the focussing reflector, the focussing reflector being oriented such that one of the one or more foci is substantially coincident with or located within the inspection zone.

Various embodiments of the focussing reflector have been envisaged. In one such embodiment the focussing reflector comprises a paraboloidal reflector having an internal reflective surface of paraboloidal-shape. The flow of particles will thus flow through the focus of the paraboloidal reflector at which the electromagnetic radiation is conversed. In another embodiment of the invention the focussing reflector may have an ellipsoidal reflective surface with two foci and an optical axis extending between the two foci. In particularly preferred versions of this, the flow source is oriented so that the flow of particles is aligned with the optical axis of the reflective surface. Moreover, any forms of the focussing reflector may be provided with an aperture for the passage of flow beyond the focussing reflector. Such an embodiment is particularly adapted for use in a sorting flow cytometer which collects the electromagnetic radiation produced from the particles in the flow, processes the collected electromagnetic radiation to derive predetermined information relating to each of at least some of the particles in the flow and correlates the derived information with the associated particle downstream of the inspection zone. In this way, the sorting flow cytometer can not only analyse the particles in the flow but sort the particles according to predetermined sets of selection criteria. A preferred type of sorting flow cytometer is a jet-in-air flow cytometer.

In another aspect of the present invention there is provided a flow cytometer including: a flow source to produce a flow of particles to be analysed, the flow source being adapted to direct the flow of particles through an inspection zone; an optical arrangement including a source of electromagnetic radiation, the optical arrangement adapted to direct electromagnetic radiation onto the flow of particles, at the inspection zone; a collector to collect electromagnetic radiation either produced or deflected from the particles, the collector having an internal reflective surface with an optical axis and one or more foci, wherein the collector is oriented such that the flow of particles is substantially aligned with the optical axis.

In yet another aspect of the present invention there is provided a flow cytometer including: a flow source to produce a flow of particles to be analysed, the flow source being adapted to direct the flow of particles through an inspection zone; an optical arrangement including a source of electromagnetic radiation, the optical arrangement adapted to direct electromagnetic radiation onto the flow of particles, at the inspection zone; a collector to collect electromagnetic radiation either produced or deflected from the particles, the collector having an internal reflective surface with an optical axis and one or more foci, wherein the collector is disposed such that one of the one or more foci is substantially coincident or located within the inspection zone; a processor to derive, from the collected electromagnetic radiation, predetermined information relating to each of at least some of the particles in the flow; and a correlator to correlate the derived information with the associated particle downstream of the inspection zone.

The collector may be of the same form as the focussing reflector as described in accordance with previous aspects of the invention. In fact, the collector may also comprise part of the optical arrangement adapted to direct electromagnetic radiation onto the flow of particles. In other words the collector may serve the dual function of collecting the produced electromagnetic radiation as well as reflecting the incident radiation onto the particles.

In accordance with another aspect of the present invention there is provided an analysation instrument including: a first reflector having a partial ellipsoidal shape;

a near focal point of the partial ellipsoidal shape of the first reflector; a distant focal point of the partial ellipsoidal shape of the first reflector; a central axis of the partial ellipsoidal shape defined by the near focal point and distant focal point of the partial ellipsoidal shape of the first reflector; a source of electromagnetic radiation disposed at the near focal point of the partial ellipsoidal shape capable of emitting electromagnetic radiation toward the first reflector; a second reflector having a partial ellipsoidal shape oriented relative to the first reflector so as to be capable of receiving electromagnetic radiation reflected by the first reflector; a near focal point of the partial ellipsoidal shape of the second reflector; a distant focal point of the partial ellipsoidal shape of the second reflector; a central axis of the partial ellipsoidal shape defined by the near focal point and distant focal point of the partial ellipsoidal shape of the second reflector, a flow source to produce a flow of particles to be analysed; and an inspection zone of the flow of particles located at the near focal point of the partial ellipsoidal shape of the second reflector.

In a preferred embodiment, the source of electromagnetic radiation may comprise an arc lamp. Further, a preferred relationship between the first reflector and the second reflector is that the distant focal point of the first reflector and the distant focal point of the second reflector overlap. The focal lengths of the first and second reflectors may be equivalent. Alternatively, the focal lengths of the two reflectors may be different in that the first reflector has a greater focal length than the second reflector.

The term "ellipsoidal reflector" as used in the above described aspect of the invention and in following aspects and in the following description of the invention, is understood to mean a reflector which conforms to the shape of an ellipsoid of revolution. Furthermore, the term is understood to mean a portion of a full ellipsoid of revolution such as one third of an ellipsoid of revolution with an opening at the vertex.

In referring to ellipsoids throughout this description where only a partial ellipsoid is used, the near focal point is intended to mean the focal point closest to the ellipsoidal portion being used.

In accordance with yet another aspect of the present invention there is provided a method of analysing including: utilising a first reflector having a partial ellipsoidal surface with a near focal point and a distant focal point; emitting electromagnetic radiation from a source of electromagnetic radiation positioned at the near focal point of the first reflector; reflecting electromagnetic radiation emitted by the source of electromagnetic radiation from the first reflector; utilising a second reflector having a partial ellipsoidal surface with a near focal point and a distant focal point; providing a flow of particles to be analysed; directing the flow of particles through an inspection zone; positioning the second reflector so that the near focal point of the second reflector overlaps the inspection zone and so that the second reflector is capable of receiving electromagnetic radiation reflected by the first reflector.

In accordance with another object of the present invention there is provided an analysation instrument including: a first reflector having a partial paraboloidal shape; a focal point, and a focal length of the partial paraboloidal shape of the first reflector; a parabolic axis of the partial paraboloidal shape of the first reflector; a source of electromagnetic radiation disposed at the focal point of the partial paraboloidal shape adapted to emit electromagnetic radiation toward the first reflector; a second reflector having a partial paraboloidal shape oriented relative to the first reflector so as to be capable of receiving electromagnetic radiation reflected by the first reflector; a focal point, and a focal length of the partial paraboloidal shape of the second reflector; a parabolic axis of the partial paraboloidal shape of the second reflector; a flow source to produce a flow of particles to be analysed; and an inspection zone of the flow of particles located at the focal point of the partial paraboloidal shape of the second reflector.

An arc lamp may be the source of electromagnetic radiation. It is preferred that the parabolic axes, i.e., optical axes, of the first and second paraboloidal-shapes are colinear. In one embodiment of the invention the focal lengths of the first and second reflectors may be equivalent. Alternatively the focal length of the first reflector may be greater than the focal length of the second reflector. A filter may be arranged between the focal points of the two reflectors.

In another aspect of the present invention there is provided a method of analysing including: utilising a first reflector having a partial paraboloidal surface, an optical axis and a focal point; emitting electromagnetic radiation from a source of electromagnetic radiation positioned at the focal point of the first reflector; reflecting electromagnetic radiation emitted by the source of electromagnetic radiation from the first reflector, utilising a second reflector having a partial paraboloidal surface, an optical axis and a focal point; providing a flow of particles to be analysed; directing the flow of particles through an inspection zone; positioning the second reflector so that the focal point of the second reflector overlaps the inspection zone and so that the second reflector is capable of receiving electromagnetic radiation reflected by the first reflector.

The present invention also provides, in accordance with another aspect of the invention, a nozzle including an opening for a flow of particles to flow through; a reflector coupled to the nozzle and oriented to reflect electromagnetic radiation at the flow of particles.

The reflector may take on various forms such as an ellipsoidal reflective surface or a paraboloidal reflective surface, the reflector and the nozzle may even be integral. In a preferred embodiment of the invention, the flow of particles passes through an inspection zone and a source of electromagnetic radiation is provided to illuminate the inspection zone. Where the reflective surface is of the kind having a focal point, then it is preferred that the focal point of the reflective surface overlaps the inspection zone.

In preferred forms of the invention, the reflective surface may comprise a metal shape embedded in the nozzle. Alternatively, the reflective surface may comprise a reflective coating applied to the nozzle. Suitably, the focal point of the reflective surface can be external to the nozzle. The nozzle may be adapted to receive electromagnetic radiation through the opening in the nozzle to illuminate the reflector or through the nozzle material itself, e.g. via light transmission through a glass nozzle.

In accordance with a further aspect of the invention there is provided a method of illuminating a flow of particles, the method including: providing a nozzle having a reflector coupled to the nozzle and oriented to reflect electromagnetic radiation; supplying a flow of particles; directing the flow of particles through the nozzle; reflecting electromagnetic radiation with the reflector toward the flow of particles.

Another aspect of the invention provides a flow cytometer including: a flow source to produce a flow of particles to be analysed, the flow source being adapted to direct the flow of particles through an inspection zone; an optical arrangement including a source of electromagnetic radiation, the optical arrangement adapted to direct electromagnetic radiation onto the flow of particles, at the inspection zone; a partial ellipsoidal collector to collect electromagnetic radiation either produced or deflected from the particles, the collector having an internal reflective surface of partial ellipsoidal shape with two foci and an optical axis oriented along a line between the two foci; the flow source being oriented such that the flow of particles is substantially aligned with the optical axis.

The preferred form of the flow cytometer may be a jet-in-air flow cytometer. Most preferably, the flow cytometer enables sorting through the use of electrostatic plates.

A corresponding aspect of the invention provides a method of flow cytometry including passing a flow of particles to be analysed through an inspection zone; providing a focussing reflector having one or more foci; converging electromagnetic radiation onto the flow of particles at the inspection zone by reflection from the focussing reflector and aligning the inspection zone with one of the one or more foci.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Some embodiments of the invention are discussed in "A New Optical Configuration for Flow Cytometric Sorting of Aspherical Cells", Int. Soc. Optical Engr., Proc. Of Adv. Tech. Analytical Cytology, 1997, by John C. Sharpe, Peter N. Schaare and Rainer Kunnemeyer; "Radially Symmetric Excitation and Collection Optics for Flow Cytometric Sorting of Aspherical Cells", Cytometry 29:363–370 (1997) by John C. Sharpe, Peter N. Schaare, and Rainer Kunnemeyer; and "A New Optical Configuration for Flow Cytometric Sorting of Bovine Spermatozoa by Sex", a thesis submitted to the University of Waikato for the degree of Doctor of Philosophy in Physics by Johnathan Charles Sharpe, which are hereby incorporated by reference.

Figure 1:
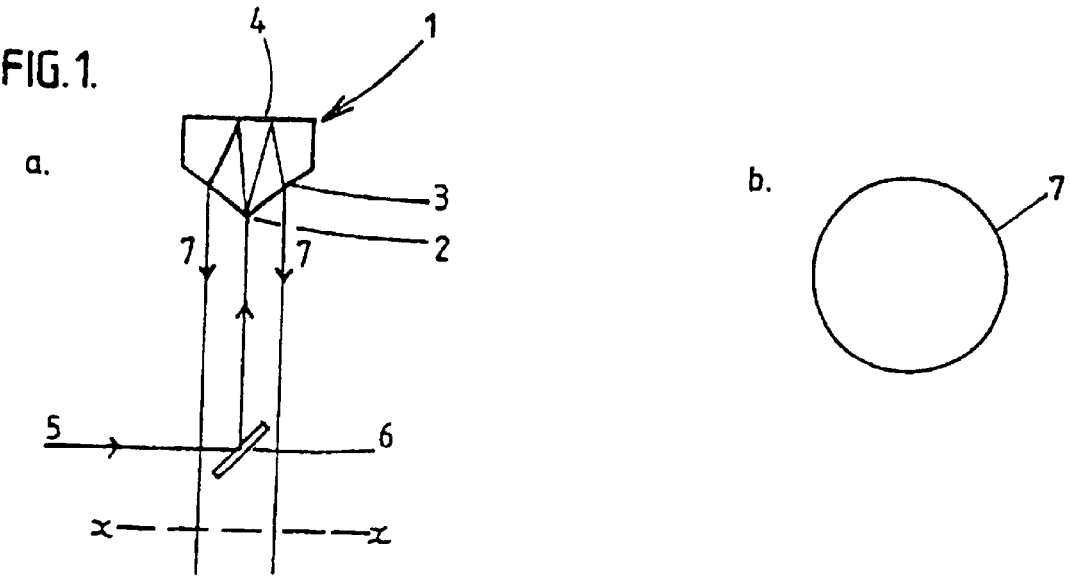
FIG. 1(a) is a cross-sectional view of one embodiment of an optical apparatus capable of producing an annular beam of electromagnetic radiation.
FIG. 1(b) is a section through the beam of FIG. 1.
FIG. 1(d) is a perspective view of one embodiment of a prism for use in the optical apparatus of FIG. 1(a)
FIG. 1(e) is a perspective view of an alternative form of a prism for use in the optical apparatus of FIG. 1(a)
FIG. 1(f) is a perspective view of an alternative prism arrangement for use in the optical apparatus of FIG. 1(a)
FIG. 1(g) is a perspective view of an alternative prism arrangement for use in the optical apparatus of FIG. 1(a)
Figure 1:
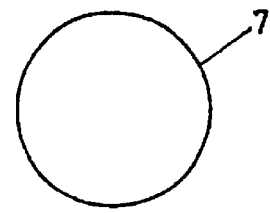

FIG. 1(a) illustrates an optical apparatus including a prism 1. The prism 1 has an apex 2 at a forward end of the prism, a right conical portion having a conical face 2, and a right cylindrical base portion contiguous with the conical portion. The base portion has a circular shaped rear end 4 with a reflective coating. An optical arrangement is provided to provide incoming electromagnetic radiation 5 such as ultra-violet light from a laser light source. The UV light 5 is directed in direction aligned with the central axis of the prism 1 onto the apex 2 of the prism 1 via a second reflector in the form of mirror 6 positioned at an angle of 45 degrees with respect to the incoming light 5 and the central axis of the prism 1. As the incoming light 5 enters the prism 1 via the apex 2 it is refracted by the prism 1 and diverges in a cone and is reflected off the rear end 4 of the lens 1. The reflected light exits the prism 1 through its conical face 3 and is projected from the forward end of the prism as an annular beam. The beam defines an enclosed cylindrical band of light having a longitudinal axis coincident with the central axis of the prism 1. FIG. 1(b) shows a cross section through the enclosed band of light. The production of a cylindrical band of light may have many uses throughout the field of optics. FIG. 1(e) illustrates the prism 1 in perspective view.

Figure 1D:
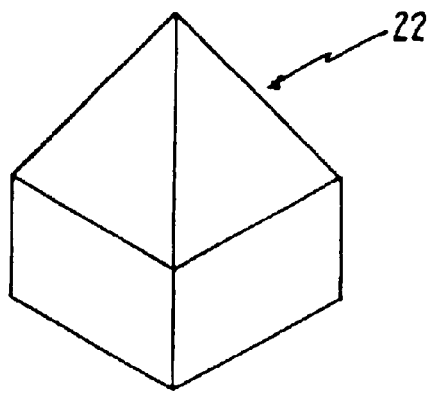
Figure 1E:
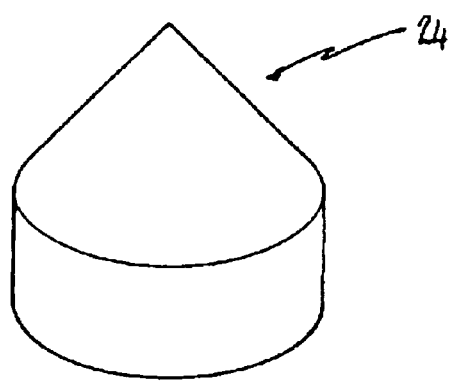

FIG. 1(d) illustrates an alternative form of prism 22. The prism 22 has a right pyramidal portion with four inclined faces meeting at an apex. A base portion is also provided which is square in cross-section, corresponding to the cross-section of the base of the pyramidal portion. The prism can be used in the same manner as prism 1 by directing incident light onto the apex of the prism in line with the central axis of the prism. However, in this embodiment, the projected light will emerge as four parallel beams equally spaced from the central axis. The number of inclined faces of the pyramidal portion may vary, provided that an even number is maintained.

Figure 1F:
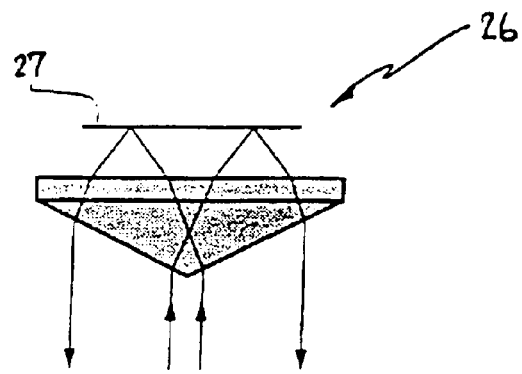

FIG. 1(f) illustrates an alternative prism arrangement in which a reflective surface may be spaced from the rear end of the conical prism shown in FIG. 1(e) or the pyramidal prism shown in FIG. 1(d). The spacing of the reflective surface 27 from the prism may be adjustable.

Figure 1G:
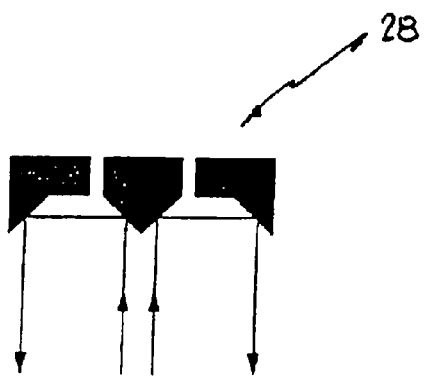

FIG. 1(g) illustrates an alternative prism arrangement known as a w-axicon or waxicon. The waxicon 28 comprises an inner conical axicon surrounded by an annular axicon concentric with the inner axicon. The reflective surfaces define a W, hence the name waxicon.

Figure 2:
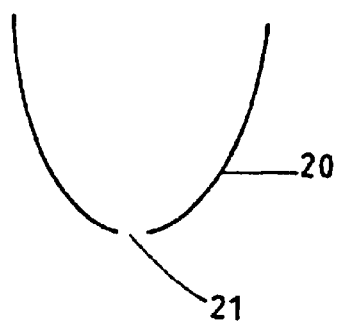
FIG. 2 is sectional view of a paraboloidal reflector.

FIG. 2 shows a paraboloidal reflector 20 in the form of a mirror having a paraboloidal-shaped internal reflective surface. The paraboloidal internal reflective surface has a focus and an optical axis running through the focus. It will be understood that the paraboloidal shaped reflective surface can have the property whereby any light which leaves the focus of the paraboloidal reflector and becomes incident on the surface of the reflector will be reflected out of the reflector 20 parallel to the optical axis. Likewise, when light which is reflected parallel to the optical axis enters and hits the reflective surface, it will be projected toward and through the focus. An aperture 21 is centrally positioned within the paraboloidal reflector 20, in line with the optical axis.

Thus, the paraboloidal reflector 20 may be used to provide multi-directional illumination of an object for analysis or inspection. By positioning the object at the focus of the paraboloidal reflector 20 and providing light incident on the surface of the reflector 20 and parallel to the optical axis of the reflector 20, the incident light can be reflected towards the object at the focus. Further, if the incoming parallel light is evenly spaced in relation to the optical axis then the light illuminating the object at the focus will be radially symmetric. The paraboloidal reflector 20 may thus be teamed with the optical apparatus shown in FIG. 1 in a manner in which the paraboloidal reflector 20 is oriented to receive the light projected from the forward end of the prism 1 with the central axis of the prism 1 aligned with the optical axis of the paraboloidal reflector 20. This particular arrangement is discussed further in connection with the flow cytometer shown in FIGS. 6, 7, 9, 10, 11, 13. However the paraboloidal reflector is not limited in its use in combination with the optical apparatus shown in FIG. 1.

Figure 3:
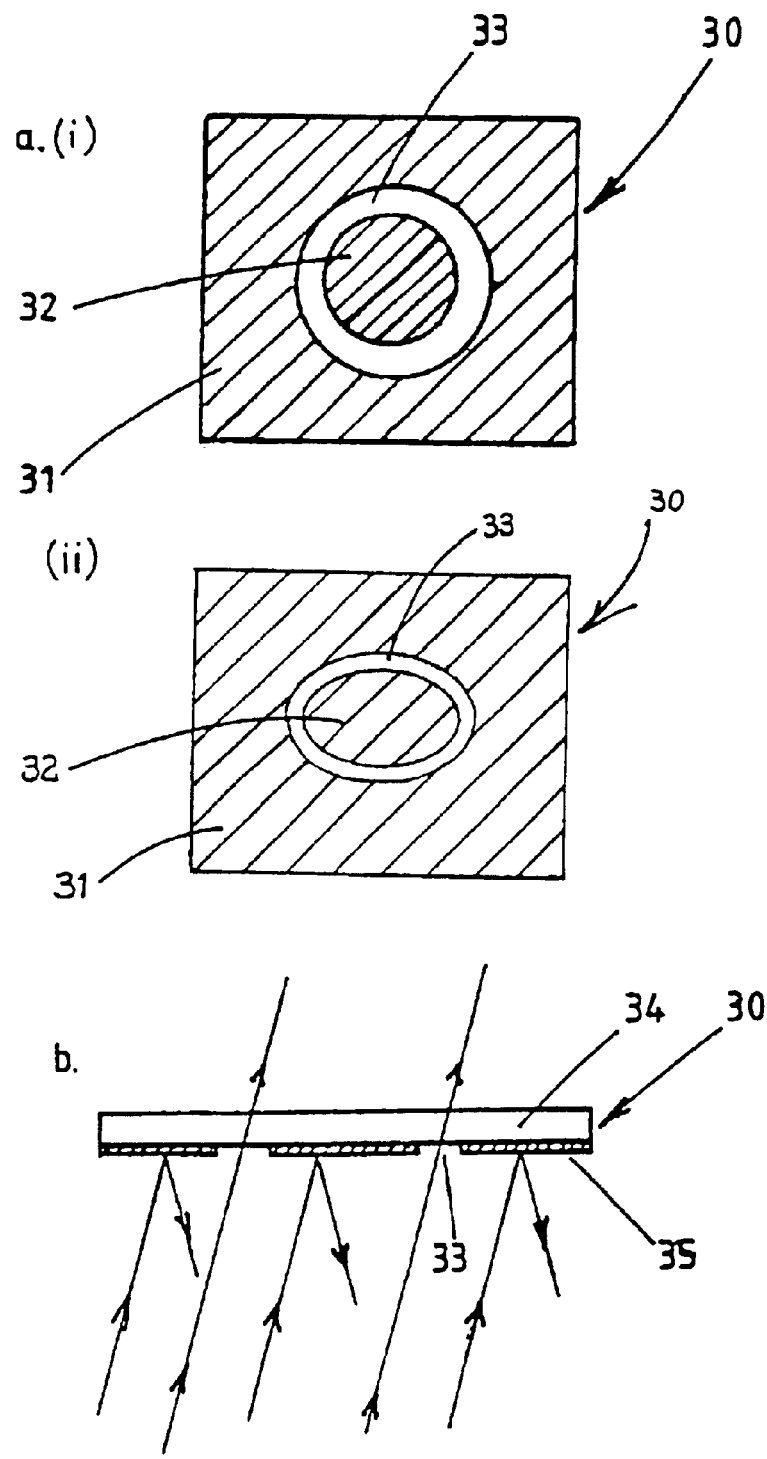
FIG. 3 shows various views though a reflector which includes transmitting and reflecting surfaces.

FIGS. 3(a) (i) and (ii) are plan views of another embodiment of the second reflector of FIG. 1 generally indicated by arrow 30. The mirror 30 includes reflective surfaces 31 and 32. The mirror 30 also includes a transmitting portion which is in the form of an annular ring 33. It should be appreciated that in some embodiments the transmitting portion 33 may be in the form of an aperture which extends through the mirror 30. However, in other embodiments such as that shown more clearly in FIG. 3(b), the transmitting portion 33 may be in the form of a transparent material, such as glass 34 which has not been covered by a reflective surface 35. As FIG. 3(b) shows, any incoming light 36 that impacts on the reflective surface 35 is reflected, whereas incoming light which impacts on the transmitting portion 33 may continue to travel substantially in the same direction The transmitting portion 33 when arranged at a 45 degree angle from which it is viewed in plan in FIG. 3(a) (i) serves to allow passage of the annular beam of light projected from the forward end of the prism. FIG. 3(a) (ii) shows a plan view of the second reflector having an egg-shaped transmitting portion 33 necessary to achieve the annular transmitting portion 33 when oriented at 45 degrees.

Figure 4:
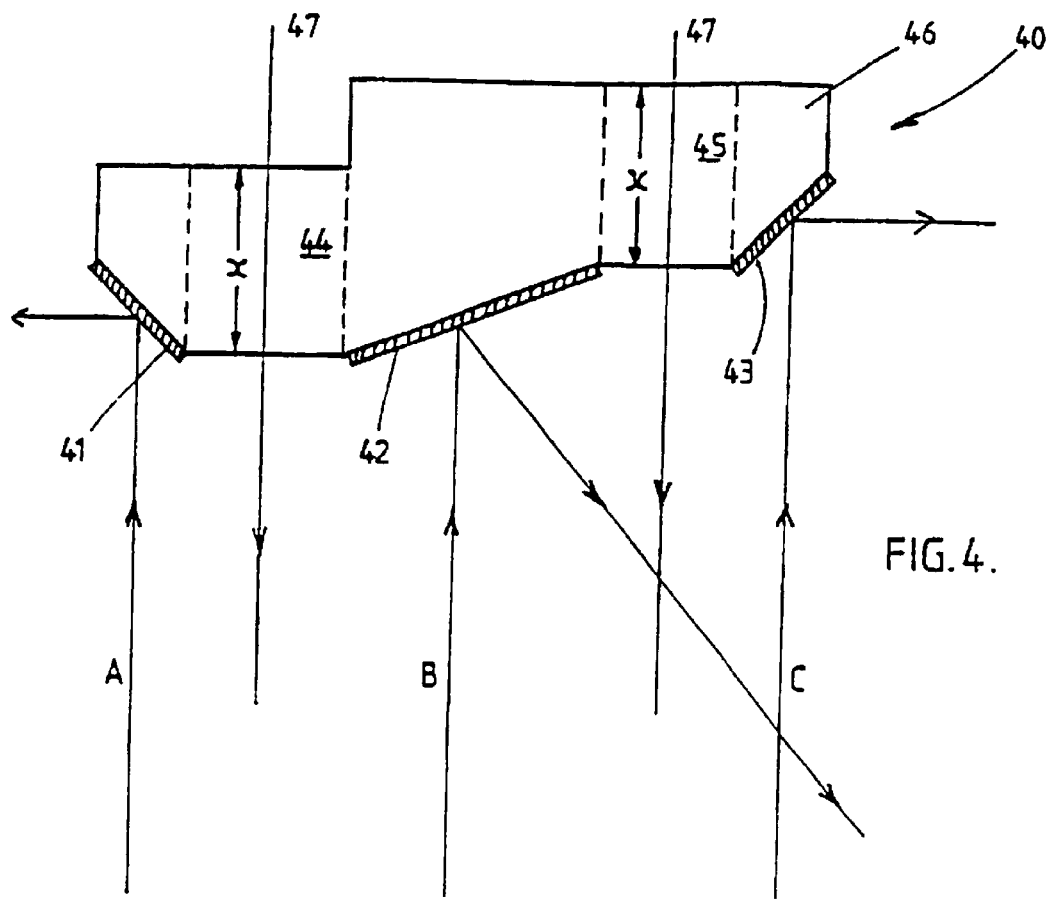
FIG. 4 is a cross-sectional view of a possible embodiment for a reflector apparatus.

FIG. 4 shows an alternative reflector apparatus generally indicated by arrow 40 which may be used to collect illumination reflected from the paraboloidal reflector 20 in FIG. 2. The reflector apparatus 40 includes a body 46 having a number of reflective surfaces 41, 42 and 43 which are positioned with respect to the detector apparatus 40 so that they may reflect any light they receive in different directions and/or at different angles.

The reflector apparatus 40 also includes within its body 46 regions 44 and 45 (both of which are bounded by dotted lines) which allow for the transmission of light 47 through the reflector apparatus 40. It should be appreciated that the regions 44 and 45 may be in the form of apertures through the body 46 or alternatively made of a transparent substance/material capable of allowing for the transmission of light. In embodiments where regions 44 and 45 are made of a transparent substance/material it will usually be desirable that the regions have the same length as shown by double headed arrow x to ensure distance travelled and refraction of the light 47 is substantially identical in both regions.

The reflective surfaces 41, 42, and 43 are capable of discriminating against the different types of light A, B and C that may be received by the reflector apparatus 40, by reflecting it in different directions and/or at different angles. Thus, the different types of light A, B and C may be reflected to suitable light detectors (not shown) for determination of the characteristics of each type of light.

Figure 5:
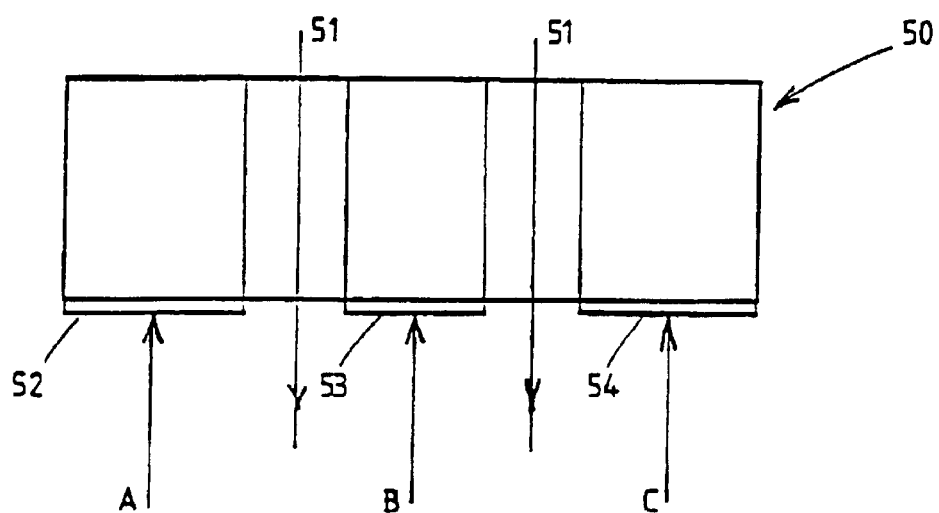
FIG. 5 is a cross-sectional view of a possible embodiment for a detector apparatus.

FIG. 5 illustrates a detector apparatus generally indicated by arrow 50 which may also be used to collect illumination from the paraboloidal reflector shown in FIG. 2. In this embodiment the detector apparatus 50 may also provide for the transmission of light 51 from a light source (not shown) in a similar manner to the reflector apparatus described above in connection with FIGS. 3 and 4. The detector apparatus 50 may also have a number of light detectors 52, 53 and 54 spatially positioned so that they may receive the different types of light A, B and C incident on the reflector apparatus 50. Thus, the spatial orientation of the light detectors 52, 53 and 54 on the detector apparatus 50 allows for the discrimination between different types of light. On the other hand, where measurement of certain light is not desired, eg. light merely reflected from the light source, such light can be allowed to travel through the transmitting portion(s) 51 of the detector apparatus.

Figure 6:
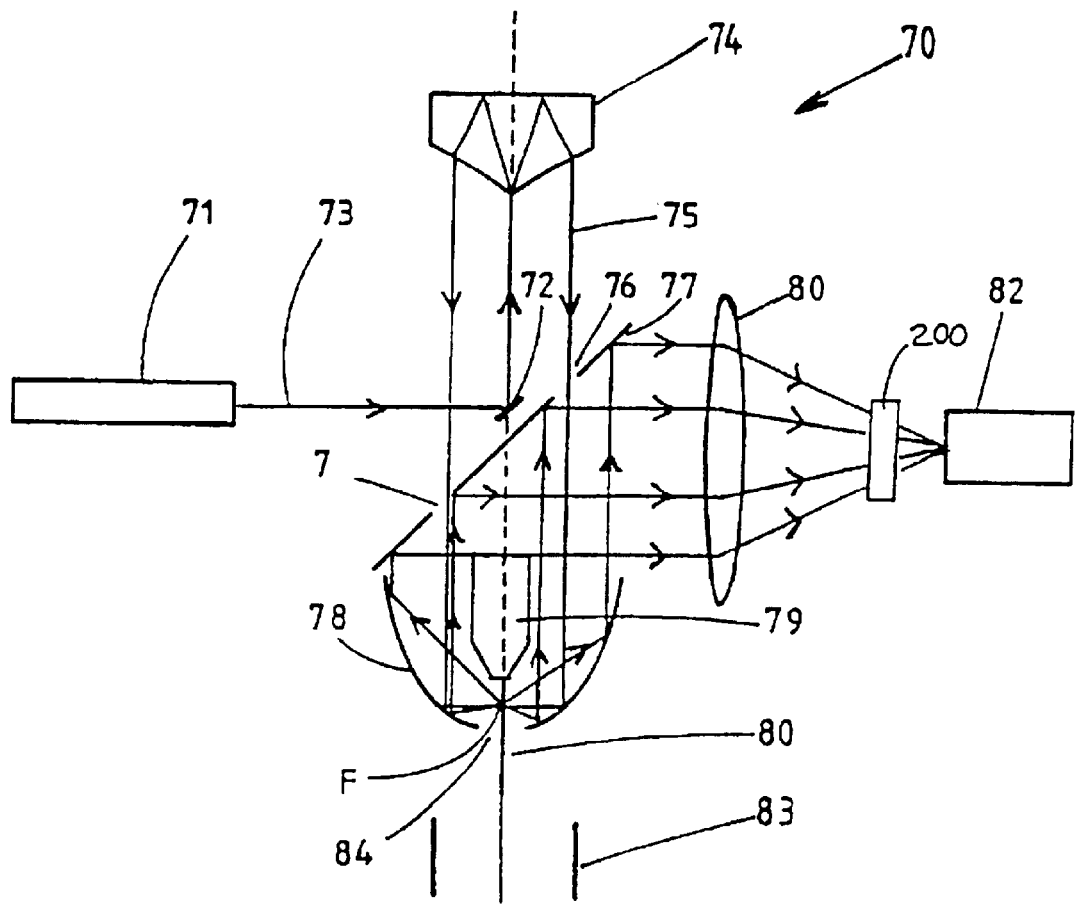
FIG. 6 is a cross-sectional view of one preferred embodiment of a flow cytometer in accordance with an aspect of the present invention.

FIG. 6 illustrates a first preferred embodiment of a flow cytometer generally indicated by arrow 70. The flow cytometer 70 includes the optical apparatus substantially as shown in FIG. 1. The optical apparatus includes an optical arrangement including a light source 71 and a mirror 72. The light source 71 produces collimated ultra-violet laser light 73 which is directed via mirror 72 to a prism 74 having a central axis. The prism 74 is configured to produce a cylinder of light 75 having a longitudinal axis coincident with the central axis of the prism. The prism may be the same as that indicated in FIG. 1(a) or (e) of the drawings. Alternatively, the prism may have a pyramidal face such as that shown in FIG. 1(d) to produce parallel beams of light evenly spaced from the central axis of the prism. The projected light 75 passes through an annular gap 76 in a second reflector 77 so as to be incident on the 45 degree point of a paraboloidal reflector/collector 78. It will be seen in the following discussion that the reflector also services as a collector. For ease of reference the paraboloidal reflector/collector 78 will be simply referred to as the paraboloidal reflector 78. The paraboloidal reflector 78 has an optical axis aligned with the central axis of the prism and a focus F lying on the optical axis.

Situated within the paraboloidal reflector 78 is a nozzle assembly 79 which delivers a particle stream 80 eg sperm cells, which is substantially aligned with the optical axis of the paraboloidal reflector and passes through an inspection zone located at the focus F. The nozzle assembly 79 delivers the sperm cells in a saline sheath solution and may utilise any of the known jet-in-air techniques to produce a laminar-flow particle stream with the sperm flowing single file through the inspection zone at F.

The paraboloidal reflector 78 is designed with two criteria in mind. Firstly, the reflector 78 should be able to withstand the corrosive environment introduced by the saline sheath environment. Secondly, the reflector should be designed to maximise reflectance of light of the UV frequency. Either of a rhodium reflective coating or an $AlSiO_2$ reflective coating on a nickel substrate were found to be effective.

The effect of the cylinder of light 75 being incident at the 45 degree point of the paraboloidal mirror 78 is that it is reflected at 90 degrees so as to form a substantially coplanar disc of light which is convergent on the focal point F of the paraboloidal reflector. Thus, this disc of light is able to interact with the particle stream 80 and illuminate the particles within the stream with substantially radially symmetric illumination.

If the particles have been stained with light-sensitive stain, the particles will fluoresce when illuminated. The use of stains is an accepted technique in sperm sexing since the number of molecules of stain bound will be equivalent to the number of molecules of DNA. This difference in uptake will yield a difference in the number of cells available for excitation and fluorescence. The difference in DNA content between X and Y sperm will yield a corresponding measurable difference in fluorescent light. Any of the known stains currently used for sperm sexing may be used. In particular, Hoechst 33342 which is of the bis-benzimidazole family shown below has been shown to provide the necessary X-Y differential resolution.

frequencies of interest. For example the dichroic mirror may be incorporated into the second reflector 77. However, if in certain applications it is desirable to measure scattered light, no filter is necessary.

It should be appreciated that instead of the single measurement detector 82 shown, an array of measurement detectors may be provided with an appropriate array of filters for measuring different forms of light. For example, the use of a second reflector in the form as that shown in FIG. 4 allows for the separation of light from different parts of the paraboloidal reflector, it being possible to apply different filters to each of the separate light parts.

Light which has not interacted with the particles may be refracted by the medium which makes up the sample stream 80 and radiate as a disc in the opposite direction to the incoming light. As the particle stream will generally have a small diameter the resulting refraction of light by the medium will not be great. Thus, this light will substantially retrace the path of the illuminating cylinder of light and exit through the annular gap 76 in the second reflector 77. This creates a simple yet effective beam dump.

It should be appreciated that supporting structures of the components of the flow cytometer 70 including sample flow tubes for the nozzle assembly may obscure parts of the path for the cylinder of light 75. However, any resulting asymmetry in the disc of light is generally negligible and the cylinder of light is therefore still considered cylindrical. Optics might even be provided to refract an incident beam around obstructions.

The amount of light measured by the photo-multiplier tube is passed to a processor, e.g., a computer (not shown) to derive predetermined information such as an association between the amount of measured light and a property of the cell from each of at least some of the particles in the flow. This information is then correlated by a correlator, such as a computer, with the corresponding particle downstream of the inspection zone to enable sorting of the particle depend-

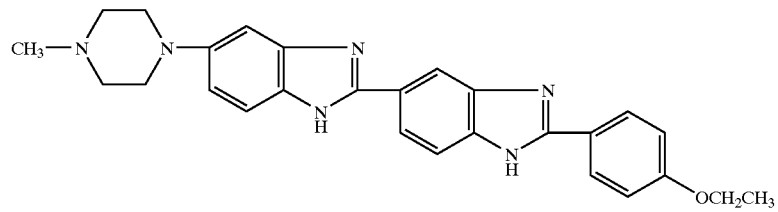

Thus, light which interacts with the particles will be scattered and/or fluoresced. This scattered and/or fluoresced light is then collected by the paraboloidal reflector/collector 78 and reflected parallel to the optical axis of the paraboloidal reflector 78. The second reflector 77 is positioned at a substantially 45 degree angle so as to reflect the scattered and/or fluoresced light towards a light detector in the form of a photo-multiplier tube 82. The second reflector 77 as appropriate may comprise the forms illustrated in FIGS. 3-5.

For the specific application of the present invention in sexing sperm, the fluorescent light is of interest and the light merely scattered from the sperm in the sample stream may be of little or no interest. The fluorescent light will be of a different frequency and the separation of the two frequencies can be achieved through the use of a high pass filter 200 positioned before the photo-multiplier tube 82. Alternatively, the separation of frequencies may be achieved through the use of a dichroic mirror to reflect only those ing whether it meets certain selection criteria. For example, male and female sperm may be sorted by sex.

The flow sorting technique uses electrostatics to charge and deflect a cell containing droplet as it passes through an electric field. The droplet is created by a mechanical oscillation applied through a piezo-electric transducer thus perturbing the sample stream as it exits the nozzle 79. Each individual droplet can be charged depending on the characteristics of its contained particle just prior to break-off by application of a voltage to the carrier fluid. Depending on its charge, the droplet will be deflected from its normal gravitational trajectory by oppositely charged plates 83. To incorporate droplet sorting it may be necessary to provide a means by which to view the stream so as to count the number of droplet spacings between the inspection point (ie. the focal point F) and the break-off point of the droplets. This can usually be achieved by inserting a small periscope through the aperture 84 in the base of the paraboloidal reflector 78. Droplets which are not electrostatically deflected from the central path are collected directly below and flushed to waste.

Figure 7:
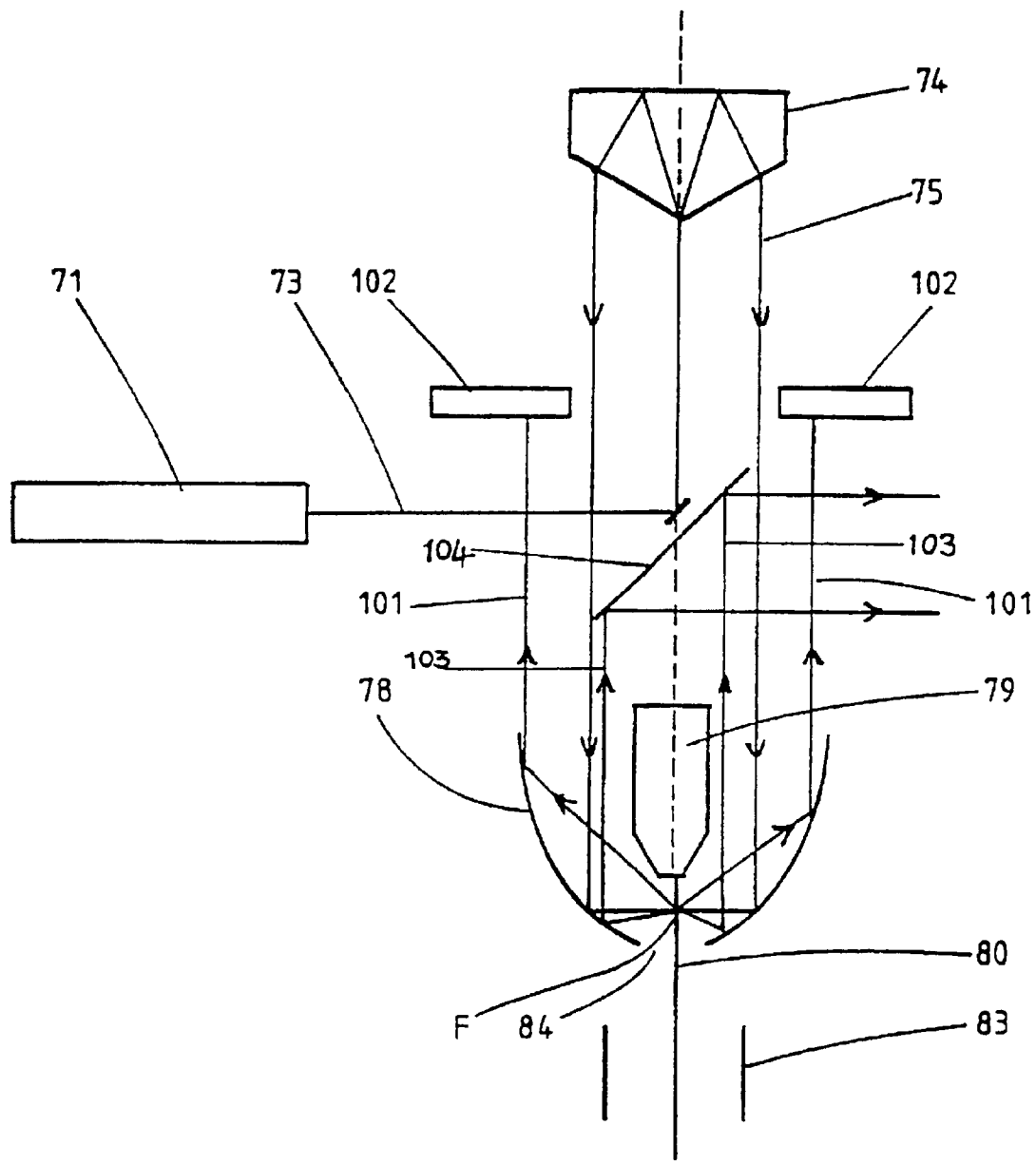
FIG. 7 is a cross-sectional view of a second embodiment of a flow cytometer in accordance with an aspect of the present invention.

In FIG. 7 there is provided an alternative flow cytometer generally indicated by arrow 100, this flow cytometer being substantially similar to the flow cytometer 70 shown in FIG. 6. Therefore, for ease of reference, similar numbering has been used to illustrate the components used in this embodiment.

The major difference with this embodiment shown in FIG. 7 is that only light 101 collected from the upper regions of the paraboloidal reflector are received by the photomultipliers 102. Accordingly, the second reflector 77 need not be of the type discussed in the previous embodiment. Instead, only a continuous mirror confined within the cylindrical beam 75 need be used to reflect away the forward scattered and/or fluoresced light 103.

On the otherhand, it should also be readily appreciated that where it is only desirable to consider forward scattered and/or fluoresced light, light measurement detectors may be suitable positioned so that they only receive this light.

During experimentation, it was found that an increase in sample to sheath differential pressure resulted in increased positional uncertainty of the particles through the focus, which results in a difference in illumination, and therefore fluorescence emission. There are a number of possible solutions which may be used either singly or in combination to broaden the focus around the sample stream.

The radial optics deliver a convergent disk of light at the excitation wavelength to the inspection point. Adjusting the vertical dimension of the radial focus is relatively simple if a concave or convex element is positioned in the laser beam in front of the axicon. However, broadening the focus laterally, while retaining sufficient light intensity at the focus for stain excitation and fluorescence, is not trivial.

To laterally broaden or defocus the radial focus requires that the illumination light cylinder be altered to cause divergence tangentially around its circular cross-section. This would result in a lateral displacement of the incoming light disk thereby broadening the intensity distribution of the focal area. Some optical elements were proposed to perform this function. The first optical element would take the form of a radially etched diffraction grating. Such a component would successfully achieve the goal of lateral displacement with a minimal dispersive effect in the vertical profile of the focus. The second optical element is a light shaping diffuser element. Implementation of this element into the radial optics design would result in both vertical and lateral focus broadening. Other options include a diffractor or a cylindrical lens causing the beam to diffract sideways and broaden the focus.

Another approach is to use the focussing characteristics of the laser beam which is a Caussian beam where the depth of focus 1 is proportional to the focal length f and inversely proportional to the beam diameter D. The variable L is defined as the half-height width of the flex density profile as plotted along the optical axis. Thus, an increase in the focal length of the paraboloidal reflector will cause an increase in d. Also, decreasing the diameter of the illuminating laser beam will bring about an increase in d.

In another embodiment of the invention, paraboloidal and ellipsoidal configurations of reflectors can be used to provide illumination of an inspection zone of a linear flow of particles. One distinct advantage of this type of system is the ability to use a low cost arc lamp to replace the more expensive lasers commonly used in instruments of this type.

Lasers are preferred in some devices because of the intensity of light that they can deliver. However, they have the disadvantage of only providing a specific wavelength of electromagnetic radiation. Arc lamps, however, are less expensive and can provide many different wavelengths of electromagnetic radiation in their emissions. Then, the proper wavelength can be selected by use of an inexpensive filter which filters out the undesired wavelengths of electromagnetic radiation.

Figure 8:
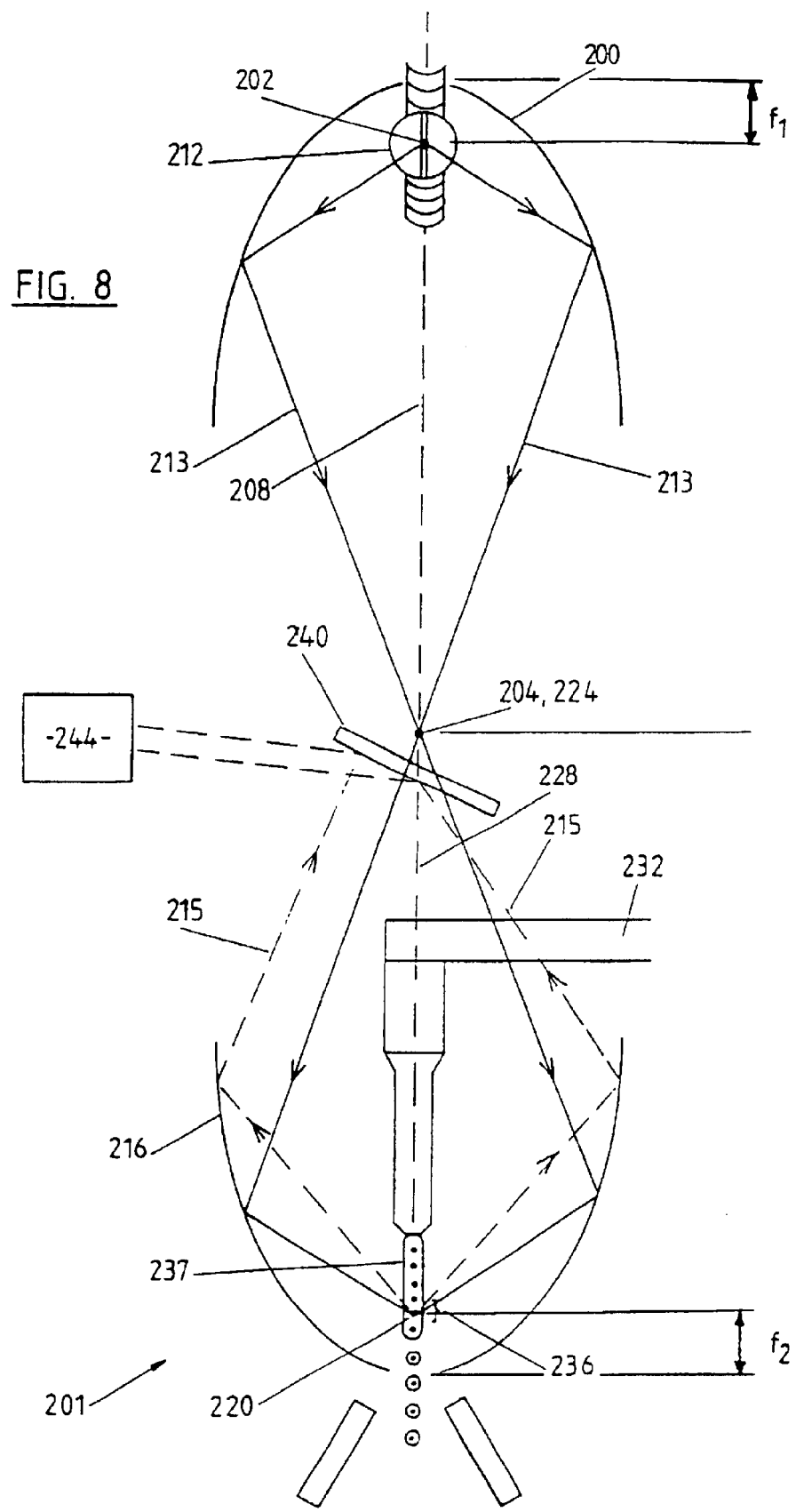
FIG. 8 is a cross-sectional view of a third embodiment of a flow cytometer in accordance with an aspect of the present invention.

Referring now to FIG. 8, an ellipsoidal embodiment of the invention can be seen. FIG. 8 shows an analysation instrument 201, such as a flow cytometer, in which a first reflector 200 having a partial ellipsoidal shape is disposed above a flow source which produces a flow 237 of particles to be analysed. The reflector can be referred to as a partial ellipsoidal reflector as it is essentially a halved ellipsoid. Nevertheless, it is understood that given the contour of its surface it is recognized as ellipsoidal or similarly having a partial ellipsoidal shape. This first reflector 200 has both a near focal point 202 disposed near the top of the ellipsoid shown in FIG. 8 and a distant focal point 204 disposed below the partial ellipsoidal shape in FIG. 8. A central axis 208 of the partial ellipsoidal shape is defined by these two focal points.

A second reflector 216 can be disposed or oriented below the first reflector. Again, the second reflector can have a partial ellipsoidal shape. Furthermore, the partial ellipsoidal shape can have a near focal point 220 disposed near the bottom of FIG. 8 and a distant focal point 224 disposed overlapping or coincident with the distant focal point 204 of the first reflector. In addition, the partial ellipsoidal shape of the second reflector can have a central axis 228 defined by its near and distant focal points. Preferably, the central axis 208 of the first reflector is substantially aligned with the central axis 228 of the second reflector.

A source of electromagnetic radiation, such as an arc lamp 212 can be disposed at the near focal point of the first reflector 200. Due to the properties of an ellipsoid, electromagnetic radiation emitted by the source of electromagnetic radiation from the near focal point 202 and incident upon the first reflector 200 can be reflected back to the distant focal point of the first reflector. When the distant focal point 204 of the fist reflector and the distant focal point 224 of the second reflector are coincident and the central axis 208 of the first reflector and the central axis 228 of the second reflector are collinear, this reflected light can continue on a path such that it is incident upon the second reflector 216. The second reflector 216 can then reflect the light which travelled through the distant focal point 224 of the second reflector to the near focal point 220 of the second reflector. In this fashion a real image of the source of electromagnetic radiation located at the near focal point 212 of the first reflector is created at the near focal point 220 of the second reflector 216. Therefore, a very intense light source can be concentrated on the inspection zone 236 of the linear flow of particles when the inspection zone is located at the near focal point 220 of the second reflector. Furthermore, this allows an arc lamp to be used—as a source with collimated beams, such as a laser, is unnecessary due to the ability of the reflectors to create a real image of the source of the electromagnetic radiation. Plus, a filter, such as a dichroic filter 240, can be used to filter out any wavelengths of undesired electromagnetic radiation.

When illuminated particles fluoresce, the fluorescence 215 can be reflected by the second reflector back towards a reflective surface, such as dichroic filter 240 which reflects the fluorescence to detector housing 244 to be detected.

Because of the ellipsoidal geometry a converging set of beams is created—thus, there is no need for optics to focus the fluorescence on the detector. FIG. 8 also shows that a stream of cells can be deflected for sorting or analysation purposes as they fall through an opening in the second reflector 216.

In FIG. 8, the first reflector and second reflector are shown having focal lengths of f1 and f2 respectively. When these focal lengths are equivalent and the distant focal points are coincident and the central axes are aligned as shown, the real image of the arc lamp will be the same size as the actual arc lamp. However, in some cases it is desirable to shrink the size of the real image of the arc source. This is the case when there is a possibility of two cells being very close to one another in the inspection zone of the stream. In such a case, it can be important to reduce a real image so that incident radiation is incident upon only the cell under analysation and not a second cell nearby. This prevents fluorescence from a second cell which might give an incorrect analysis. There is more likelihood of cells being close by when the throughput of the analyser is increased.

The arrangement of FIG. 8 could be used with only the bottom reflector and an alternative light source to illuminate the flow of particles. This might involve a laser directed at the flow of particles or off the reflective surface of the ellipsoidal reflector 216. This is a unique arrangement in flow cytometry, because the flow of particles is aligned coaxially with the central axis of the ellipsoidal reflector 216 to pass through the near focal point of the ellipsoidal reflector 216. After the flow of particles passes through the focal point at which the particles are irradiated with electromagnetic radiation for the purpose of analysation, they can be sorted based upon their identifying characteristics. Electrostatic plates can be provided and disposed below the opening in the ellipsoidal reflective surface to deflect the particles as they pass close to or between the electrostatic plates. This embodiment is particularly unique in jet-in-air types of flow cytometers.

Figure 9:
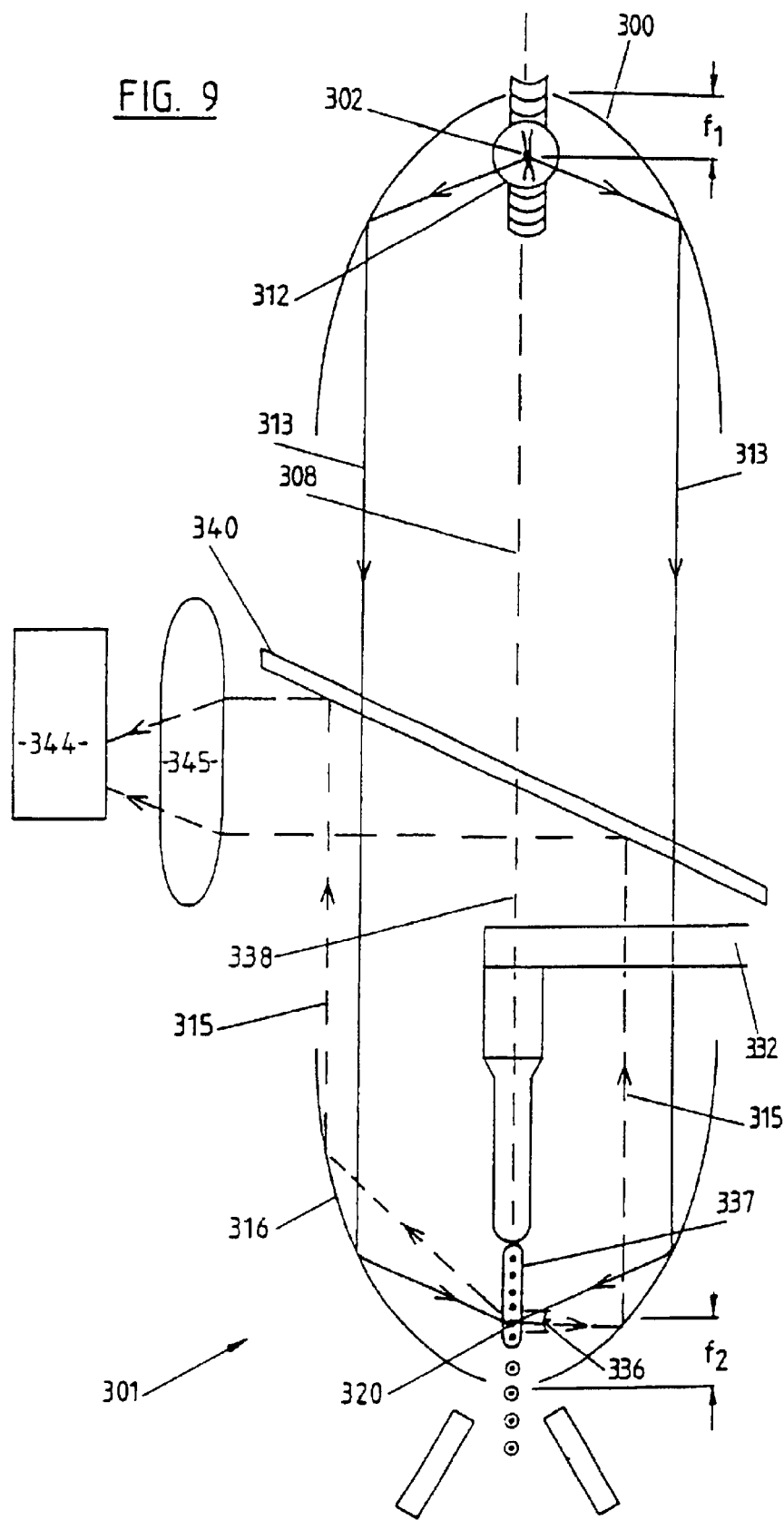
FIG. 9 is a cross-sectional view of a fourth embodiment of a flow cytometer in accordance with an aspect of the present invention.

In FIG. 9 a similar arrangement to that shown in FIG. 8 can be seen, the major difference being that paraboloidal shapes are being used for the reflectors. A first reflector 200 having a partial paraboloidal shape, a focal point (or focus) 302 is disposed to reflect electromagnetic radiation from a source of electromagnetic radiation, such as arc lamp 312. The source of electromagnetic radiation can be positioned at the focus of the paraboloid such that all emissions originating from the focus and incident on the partial paraboloid are reflected in collimated beams 313 toward a second reflector 316. The first reflector 300 and the second reflector 316 each have parabolic axes 308 and 338 respectively. These axes can be aligned such that a real image of the electromagnetic source appears at the focal point (or focus) 320 of the second reflector 316. A flow source 332 can provide a flow of particles 337 that flows through the focal point 320 of the second reflector 316. The portion of the flow of particles that flows through the focal point can be referred to as the inspection zone 336 upon which the electromagnetic radiation is focused so as to analyse a cell falling through the inspection zone.

When the incident electromagnetic radiation is incident upon a cell in the inspection zone, the stained cell can be caused to fluoresce. This fluorescence 315 can then be reflected by the second reflector 316 toward a reflector, such as dichroic mirror 340, which directs the fluorescence toward an optical apparatus 345 that focuses the fluorescence on a detector 344.

Once again, selection of equivalent focal lengths for the first reflector f1 and second reflector f2 will provide a real image of the arc lamp of the same size at the focal point of the second reflector. Similarly, choosing a focal length for the second reflector that is smaller than the focal length of the first reflector will result in a smaller image that will help prevent error when large throughput of cells is desired and consequently cells are close together at the inspection zone.

In FIGS. 8 and 9, one can see that plates can be provided to sort cells as they exit the ellipsoidal or paraboloidal shapes.

Figure 10:
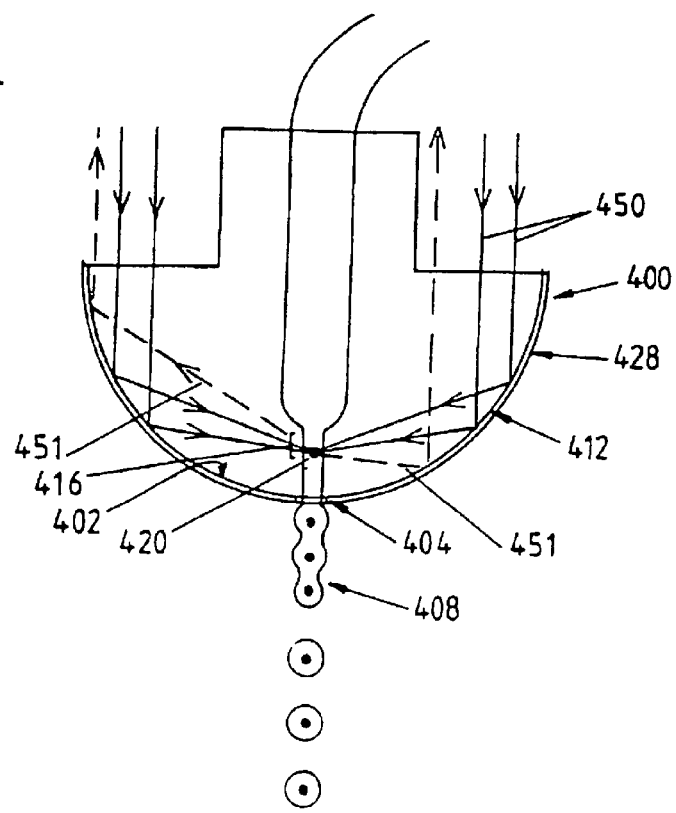
FIG. 10 is a cross-sectional view of a fifth embodiment of a flow cytometer in accordance with an aspect of the present invention.

In another embodiment of the invention, a nozzle 400 can be provided with a reflector coupled to the nozzle itself. In fact, the reflector can even be integral to the nozzle. This presents a significant advantage to the user of the analysing apparatus as there is no need for alignment of the components since the coupling can accomplish that task. Referring to FIGS. 10, 11, 12 and 13 one can see how various embodiments of such a nozzle could be implemented. In FIG. 10, a paraboloidal nozzle is shown. The nozzle can be manufactured of a material such as glass that permits the transmission of electromagnetic radiation, such as visible light. Incident beams of electromagnetic radiation from a source of electromagnetic radiation, such as a laser source 520 in FIG. 11 pass through the nozzle body and are incident on a reflector 402. The reflector 402 is coupled to the nozzle itself rather than existing separate from the nozzle. An opening 404 can be provided in the nozzle to allow a flow of particles 408 to flow through. The reflector 402 can be oriented to reflect the incident a electromagnetic radiation at the flow of particles 408.

Two possible shapes which can be used for the reflective surface of the reflector are a paraboloid and an ellipsoid. In FIG. 10, a paraboloidal reflective surface 412 is shown while in FIG. 11, an ellipsoidal reflective surface 512 is shown. As explained elsewhere, an inspection zone 416 can overlap a focal point(s) of the reflective surface, such as focal point 420 of the paraboloid of FIG. 10 to produce the desired reflection patterns.

Figure 11:
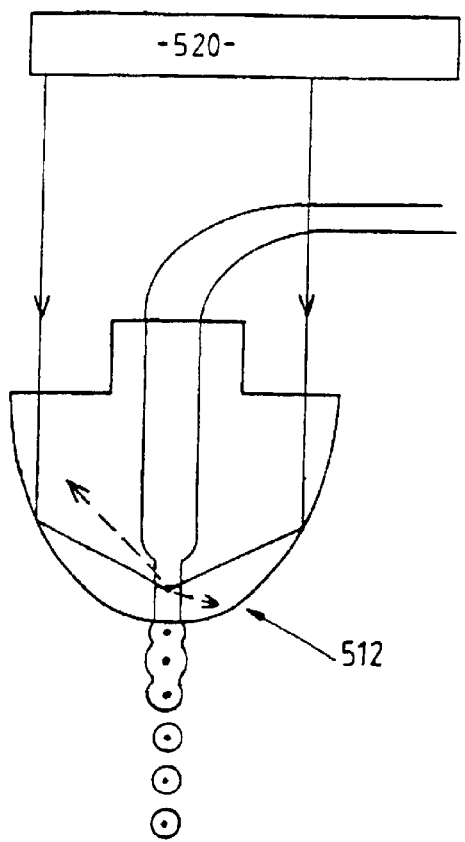
FIG. 11 is a cross-sectional view of a sixth embodiment of a flow cytometer in accordance with an aspect of the present invention.

The nozzle can be used with a source of electromagnetic radiation, such as a laser source 520 as shown in FIG. 11. However, it is also envisioned that an arc lamp or other source could be used as well. The source of electromagnetic radiation emits beams 450 which can be directed at the reflective surface. When the electromagnetic radiation is incident upon a cell under analysis, fluorescence is created as shown by beams 451.

Figure 12:
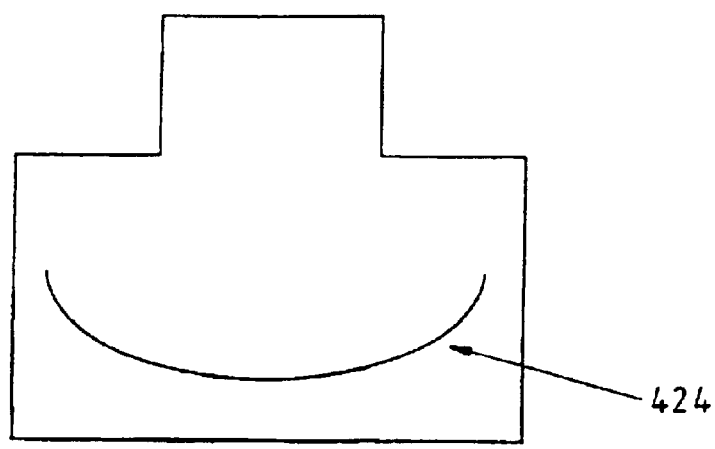
FIG. 12 is a cross-sectional view of a reflector incorporated into a flow nozzle design according to an aspect of the present invention.

To create the reflective surface, a variety of designs are possible. First, the nozzle body could be shaped in a paraboloidal or ellipsoidal shape and then coated with a reflective material 428 applied to the nozzle surface. Additionally, a reflector, such as a metal reflector 424 could be inserted or embedded in the nozzle body as shown in FIG. 12. It might even be possible to rely on refractive properties which cause internal reflection or even total internal reflection.

Figure 13:
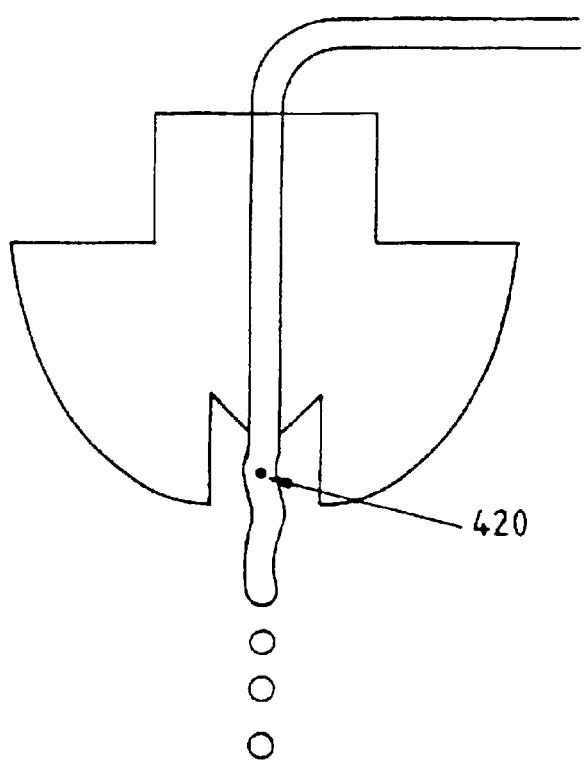
FIG. 13 is a cross-sectional view of a seventh embodiment of a flow cytometer in accordance with an aspect of the present invention.

In FIG. 13, an embodiment is shown in which the nozzle is shaped such that the focal point 420 of the reflective surface is external to the nozzle. External is intended to means outside of or away from the nozzle border, In such an embodiment, electromagnetic radiation could be directed at the focal point without needing to traverse through the nozzle body.

Figure 14:
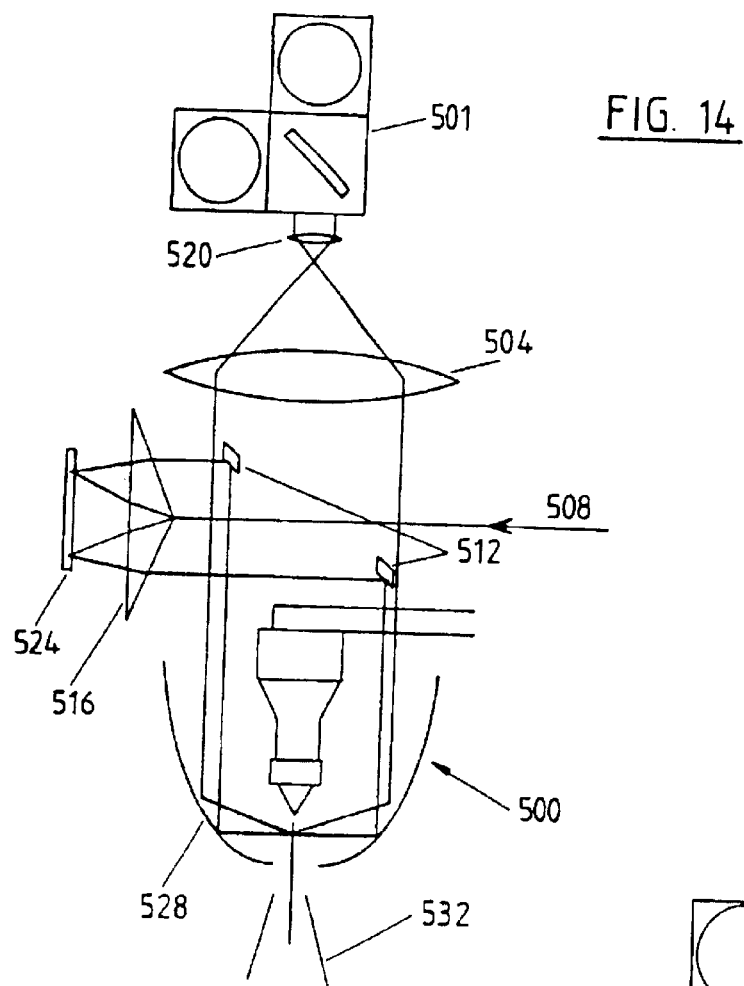
FIG. 14 is a cross-sectional view of an eighth embodiment of a flow cytometer in accordance with an aspect of the present invention.
Figure 15:
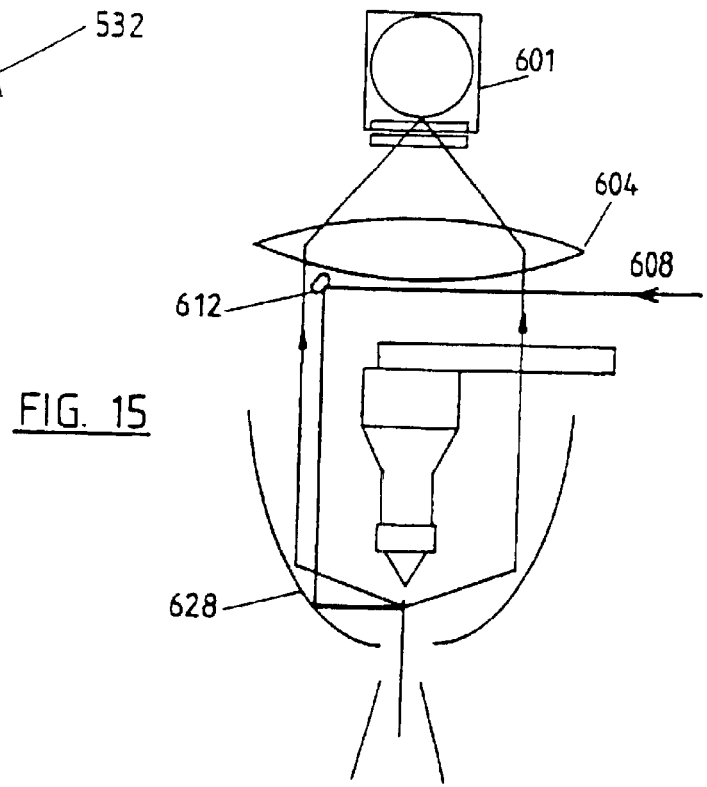
FIG. 15 is a cross-sectional view of a ninth embodiment of a flow cytometer in accordance with an aspect of the present invention.

Alternative embodiments of the invention can be seen in FIGS. 14 and 15. In FIG. 14, the radial optics configuration for a flow cytometer 500 can combine 360 degree radial illumination and radially symmetric collection of fluorescence from particles or cells as they pass through the inspection point A glass cone 516 and a paraboloidal reflector 528 can be used. The optical beam of a laser 508 can be steered onto the point of the glass cone. The beam can then be refracted into a divergent cone of light which is retro-reflected to produce a cylinder of laser light which encircles and is antiparallel to the input beam. This light cylinder can then be reflected by a 45 degree elliptical ring mirror 512 and aligned parallel to the optical axis of the paraboloidal reflector 528. The angle of incidence of the cylindrical beam at the reflector is 45 degrees, causing the beam to form a coplanar convergent disk perpendicular to and focused on the sample stream.

Stained cells can be carried by the sample stream through the radial excitation focus and caused to fluoresce. Much of the fluorescence can be collected by the paraboloidal reflector and projected out in a collimated beam onto an aspheric condensing lens 504. The lens can focus the fluorescent light to a spot which is imaged by a microscope objective 520 into a phomultiplier tube (PMT) 501 and filter housing. Optical alignment of specimens flowing through the focal region of the paraboloidal reflector can be achieved by adjusting the flow cell position to maximise fluorescent signals from calibration microspheres. The paraboloidal reflector can have a hole or opening in the base through which the sample stream can exit and where a jet observation camera and droplet sorting mechanism 532 can be situated.

In FIG. 15, a simplified version of the geometry of FIG. 14 is shown. The fluorescence collection elements can be retained to provide radially symmetric detection of cells as they pass through the inspection point of the flow cytometer. Excitation of cells can be performed by steering a laser beam 608 onto the paraboloidal reflector 628 at an incidence angle that results in beam delivery from one direction similar to standard flow cytometer illumination. This can be accomplished by reflecting the beam off mirror 612. Detection of cells can be performed by a paraboloidal reflector and aspheric lens combination. A single PMT, for example with a 400LP filter, can be positioned to collect all of the light focused by the aspheric lens. An additional neutral density filter (ND=1.3) can also be used to prevent saturation of the detector even at low PMT amplifier voltages.

The embodiment in FIG. 15 is particularly useful as it does not require as extensive an alignment of optics as is required in other embodiments. An ellipsoidal collector could also be used to deliver the laser light reflected from an adjusted mirror 612 and to reflect fluoresence to be collected at the PMT. The embodiments in FIGS. 15 and 16 are particularly advantageous because of the simplistic substantially coaxial alignment of the reflector with the detector.

It should be appreciated that the embodiments described in this description rely on physical arrangements that may not permit total or perfect collection, transmission, symmetry, reflection, alignment, etc. due to physical limitations of mirrors, optics and physical orientation of equipment. In view of these limits, such properties still may be considered at the very least as substantial.

Aspects of the present invention have been described by way of example only and it should be appreciated that modifications and additions may be made thereto without departing from the scope thereof.

What is claimed:

1. An analysation instrument including:
   a. a flow source to produce a flow of particles to be analysed;
   b. a source of electromagnetic radiation; and
   c. a reflector adapted to reflect at least a portion of the electromagnetic radiation at the flow of particles to illuminate the flow of particles,
   wherein the reflector is also adapted to collect and to reflect, to an optical configuration, at least a portion of any electromagnetic radiation produced as a result of the illumination of the flow of particles,
   wherein said optical configuration includes a sensor adapted to sense the electromagnetic radiation produced as a result of the illumination of the flow of particles,
   wherein the reflector has in internal surface that has an optical axis, and
   wherein the flow source is adapted to substantially align the flow with the optical axis of the internal surface of the reflector.

2. The analysation instrument of claim 1 wherein the reflector has an internal reflective surface which is paraboloidal in shape.

3. A method of analysing including the steps of:
   a. providing a flow of particles to be analysed;
   b. providing a source of electromagnetic radiation;
   c. reflecting with a reflector at least a portion of the electromagnetic radiation to illuminate the flow of particles;
   d. collecting with the reflector at least a portion of any electromagnetic radiation produced from the illumination of the flow of particles;
   e. reflecting with the reflector at least the portion of any electromagnetic radiation produced from the illumination of the flow of particles; and
   f. sensing a portion of the electromagnetic radiation produced from the illumination of the flow of particles
   wherein the reflector has an internal surface that has an optical axis, and
   wherein said step of providing a flow of particles to be analysed comprises the step of providing a flow of particles that is substantially aligned with the optical axis of the internal surface of the reflector.

4. The method of claim 3 wherein the reflector has an internal reflective surface which is paraboloidal in shape.

5. A flow cytometer including:
   a. a flow source to produce a flow of particles to be analysed, the flow source being adapted to direct the flow of particles through an inspection zone;
   b. an optical arrangement including a source of electromagnetic radiation, the optical arrangement adapted to direct electromagnetic radiation onto the flow of particles, at the inspection zone through use of a reflector;
   wherein said reflector collects and reflects electromagnetic radiation either produced or deflected from the particles, the reflector having an internal reflective surface with an optical axis and one or more foci,
   wherein the reflector is disposed such that one of the one or more foci is substantially coincident or located within the inspection zone;
   c. a processor to derive, from the collected electromagnetic radiation, predetermined information relating to each of at least some of the particles in the flow; and
   d. a correlator to correlate the derived information with the associated particle downstream of the inspection zone
   wherein said flow source is also adapted to substantially align the flow with the optical axis of the internal surface of the reflector.

\* \* \* \* \*

UNITED STATES PATENT AND TRADEMARK OFFICE
CERTIFICATE OF CORRECTION

PATENT NO.   : 6,819,411 B1
DATED        : November 16, 2004
INVENTOR(S)  : Jonathan Sharpe and Peter Niven Schaare It is certified that error appears in the above-identified patent and that said Letters Patent is hereby corrected as shown below:

Column 22,
Line 9, change the word "in" to the word -- an --.

Signed and Sealed this

Seventeenth Day of May, 2005

JON W. DUDAS
*Director of the United States Patent and Trademark Office*